(12) United States Patent
Yokoyama

(10) Patent No.: US 10,988,878 B2
(45) Date of Patent: Apr. 27, 2021

(54) OVERLOCK SEWING MACHINE

(71) Applicant: JANOME SEWING MACHINE CO., LTD., Tokyo (JP)

(72) Inventor: Ushio Yokoyama, Tokyo (JP)

(73) Assignee: JANOME SEWING MACHINE CO., LTD., Tokyo (JP)

(*) Notice: Subject to any disclaimer, the term of this patent is extended or adjusted under 35 U.S.C. 154(b) by 128 days.

(21) Appl. No.: 16/565,233

(22) Filed: Sep. 9, 2019

(65) Prior Publication Data

US 2020/0002864 A1 Jan. 2, 2020

Related U.S. Application Data

(63) Continuation of application No. PCT/JP2018/009825, filed on Mar. 13, 2018.

(30) Foreign Application Priority Data

Mar. 24, 2017 (JP) .............................. JP2017-059812
Apr. 28, 2017 (JP) .............................. JP2017-089319

(51) Int. Cl.
   *D05B 1/20* (2006.01)
   *D05B 1/12* (2006.01)
   (Continued)

(52) U.S. Cl.
   CPC ................. *D05B 1/20* (2013.01); *D05B 1/12* (2013.01); *D05B 37/06* (2013.01); *D05B 73/12* (2013.01)

(58) Field of Classification Search
   CPC ... D05B 1/12; D05B 1/14; D05B 1/18; D05B 1/20; D05B 37/06; D05B 37/063; D05B 73/12
   See application file for complete search history.

(56) References Cited

U.S. PATENT DOCUMENTS 4,267,786 A * 5/1981 Hanyu ..................... D05B 1/12
                                                      112/163
6,101,960 A * 8/2000 Ebata ................... D05B 37/063
                                                      112/122
(Continued)

FOREIGN PATENT DOCUMENTS

JP      H10-235046 A     9/1998
JP      2005-168939 A    6/2005
(Continued)

OTHER PUBLICATIONS

International Search Report issued in PCT/JP2018/009825 dated Jun. 12, 2018 with English Translation (4 pages).
(Continued)

*Primary Examiner* — Nathan E Durham
(74) *Attorney, Agent, or Firm* — Nakanishi IP Associates, LLC

(57) ABSTRACT

An overlock sewing machine includes an operating shaft that is slidable between first and second positions, and configured such that interlock switching and position switching mechanisms are operated when it is turned. The interlock switching mechanism includes a rotor that is rotatable together with the operating shaft as a single unit, an interlock switching member, and a first engagement target portion formed in the rotor. In the interlock state, setting the operating shaft to the first position engages an engagement portion of the interlock switching member with the first engagement target portion, which restricts operating shaft rotation. Sliding the operating shaft to the second position releases the engagement state between the engagement and first engagement target portions, enabling rotation of the operating shaft.

7 Claims, 18 Drawing Sheets

(51) Int. Cl.
*D05B 37/06* (2006.01)
*D05B 73/12* (2006.01)

(56) References Cited

U.S. PATENT DOCUMENTS

| 8,770,123 | B2 | 7/2014 | Sugiwara | | |
|---|---|---|---|---|---|
| 2005/0126459 | A1 | 6/2005 | Ebata et al. | | |
| 2006/0191453 | A1* | 8/2006 | Yamaguchi | ............ | D05B 57/34 |
| | | | | | 112/199 |
| 2006/0230502 | A1* | 10/2006 | Sadasue | ................. | D05B 37/04 |
| | | | | | 2/275 |
| 2013/0333603 | A1 | 12/2013 | Sugiwara | | |
| 2014/0261122 | A1 | 9/2014 | Tseng | | |
| 2015/0361606 | A1 | 12/2015 | Sugiwara et al. | | |

FOREIGN PATENT DOCUMENTS

| JP | 2007-296377 A | 11/2007 |
|---|---|---|
| JP | 2015-231499 A | 12/2015 |
| JP | 6001341 B2 | 10/2016 |

OTHER PUBLICATIONS

International Search Report issued in PCT/JP2018/009824 dated May 15, 2018 with English Translation (5 pages).

* cited by examiner

OVERLOCK SEWING MACHINE

CROSS-REFERENCE TO RELATED APPLICATIONS

This application is a continuation application of International Patent Application No. PCT/JP2018/009825 filed on Mar. 13, 2018, which claims priorities to Japanese Patent Application No. 2017-059812 filed on Mar. 24, 2017 and Japanese Patent Application No. 2017-089319 filed on Apr. 28, 2017, the entire contents of which are incorporated by reference.

BACKGROUND OF THE INVENTION

1. Field of the Invention

The present invention relates to an overlock sewing machine.

2. Description of the Related Art

With an overlock sewing machine, by continuously performing cutting and sewing of a cloth, this arrangement is capable of sewing the cloth with an approximately constant distance between the edge of the cloth and the needle location position. This allows a separate cloth cutting step to be omitted. In particular, in industrial usage, this arrangement is effectively employed to provide improved production capacity.

However, as a typical usage of such an overlock sewing machine, in some cases, the user uses only the sewing function without using the cloth cutting function.

In order to support such a usage, an overlock sewing machine described in Patent document 1 listed below is configured such that, in a case in which the overlock sewing machine is to be operated to provide only the sewing function, an upper blade is retracted downward with respect to a needle plate so as to release an interlock state between the upper blade and a main shaft of the sewing machine.

Brief description will be made regarding this overlock sewing machine. The overlock sewing machine is configured including: an upper blade driving unit including a rod configured to drive an upper blade in the upper-lower direction and a second link unit (swing member); an interlock switching unit that switches the operation state to an interlock state in which the upper blade driving unit operates together with an upper blade and a release state (interlock release state) in which the interlock between the upper blade driving unit and the upper blade is released; an upper blade position switching unit that switches the position of the upper blade to a driving position (interlock position) or otherwise a retraction position; and an operating unit that synchronously operates the interlock switching unit and the upper blade position switching unit. Furthermore, a notch is formed in the rod. The above-described interlock state is set by engaging an engagement portion of the second link unit with the notch. Moreover, the upper blade position switching unit is monolithically formed with the second link unit such that they are rotated as a single unit.

With such an arrangement, upon performing the rotational operation for the operating unit, the interlock switching unit and the upper blade position switching unit synchronously operate. In this operation, the operating state is switched to the interlock state or otherwise the release state, and the arrangement position of the upper blade is switched to the driving position or otherwise the retraction position.

RELATED ART DOCUMENTS

Patent Documents

[Patent document 1]
 Japanese Patent No. 6,001,341

However, with the overlock sewing machine described in the Patent document 1 described above, in any state thereof, the operating unit can be rotationally operated at all times. Accordingly, for example, if the user inadvertently touches the operating unit, such an arrangement has the potential to cause an issue in that the state of the overlock sewing machine is switched and the arrangement position of the upper blade is switched without the user's intention.

SUMMARY OF THE INVENTION

In view of the above-described fact, it is a purpose of the present invention to provide an overlock sewing machine that is capable of preventing the state of the overlock sewing machine from switching to the interlock state or otherwise the interlock release state without the user's intention, and of preventing the position of the upper blade from switching to the interlock position or the retraction position without the user's intention.

Embodiment 1

At least one embodiment of the present invention provides an overlock sewing machine comprising: an upper blade configured such that it can be moved between an interlock position at which it is driven in an upper-lower direction together with a rotation of a main shaft and a retraction position to which it is to be retracted downward from the interlock position; a rod configured such that it extends in a direction that is orthogonal to an axial direction of the main shaft, and arranged such that one end portion is coupled to the main shaft by an eccentric cam, which allows the rod to be swung by a driving force applied by the main shaft; a swing member supported by a support shaft arranged in parallel with the axial direction of the main shaft such that it can be swung, coupled to the upper blade via another member, comprising a fitting portion configured such that it can be fitted into a fitting target portion provided to the other end portion of the rod, and configured such that, when the fitting portion is fitted into the fitting target portion, the swing member is reciprocally swung accompanying a swinging of the rod according to a rotation of the main shaft, so as to drive the upper blade in the upper-lower direction when the upper blade is set to the interlock position; an interlock switching mechanism configured to operate to switch a state to an interlock state, in which the fitting target portion is fitted into the fitting portion so as to allow the upper blade to be driven together with the main shaft, or otherwise an interlock release state, in which a fitting state between the fitting target portion and the fitting portion is released so as to release the interlock state; a position switching mechanism configured to operate such that a position of the upper blade is switched to the retraction position or otherwise the interlock position; and an operating shaft configured such that it can be slid between a first position and a second position to which it is to be slid from the first position in the axial direction, and such that, by turning the operating shaft, the interlock switching mechanism and the position switching mechanism are operated. The interlock switching mechanism comprises: a rotor provided such that it can be rotated together with the operating shaft as a single unit; an interlock switching member coupled to the fitting target portion, including an engagement portion protruding toward the rotor side, and configured to operate according to the rotation of the rotor so as to switch the state to the interlock state or otherwise the interlock release state; and a first engagement target portion formed in the rotor such that it can be engaged with the engagement portion. In the interlock state, upon setting the operating shaft to the first position, the engagement portion is engaged with the first engagement target portion so as to restrict the rotation of the operating shaft. Upon sliding the operating shaft to the second position, the engagement state between the engagement portion and the first engagement target portion is released so as to enable the rotation of the operating shaft.

Embodiment 2

At least one embodiment of the present invention also provides the overlock sewing machine. The interlock switching mechanism comprises a coupling member configured to couple the fitting target portion and the interlock switching member. The fitting target portion is rotatably coupled to one end portion of the coupling member, and the other end portion of the coupling member is provided with a coupling pin rotatably supported by the interlock switching member. When the interlock state is set, the coupling pin is arranged on the same axis as that of the support shaft.

Embodiment 3

At least one embodiment of the present invention also provides the overlock sewing machine. The interlock switching member is configured such that it can be relatively moved with respect to the rotor in the upper-lower direction. The first fitting target portion is formed in a groove structure such that it extends in the upper-lower direction and has an opening that faces an upper side in the interlock state. In the interlock state, upon setting the operating shaft to the first position, the engagement portion is inserted into an interior of the first engagement target portion. In the interlock state, upon sliding the operating shaft to the second position and turning the rotor, the interlock switching member is displaced upward so as to release the fitting state between the fitting target portion and the fitting portion.

Embodiment 4

At least one embodiment of the present invention also provides the overlock sewing machine. A second engagement target portion is formed in the rotor such that it can be engaged with the engagement portion. In the interlock release state, by setting the operating shaft to the first position, the engagement portion is engaged with the second engagement target portion so as to restrict the rotation of the operating shaft. Upon sliding the operating shaft to the second position, the engagement state between the engagement portion and the second engagement portion is released, which enables the rotation of the operating shaft.

Embodiment 5

At least one embodiment of the present invention also provides the overlock sewing machine. The second engagement target portion is formed in a groove structure having an opening that faces the outer side in a radial direction of the rotor, and is arranged with an offset along a circumferential direction of the rotor with respect to the first engagement target portion. In the interlock release state, by setting the operating shaft to the first position, the engagement portion is inserted into an interior of the second engagement target portion.

Embodiment 6

At least one embodiment of the present invention also provides the overlock sewing machine. The operating shaft is forced toward the first position side by a shaft force-applying member.

Embodiment 7

At least one embodiment of the present invention also provides the overlock sewing machine. The operating shaft is configured to be turned in the same rotational direction when the interlock switching mechanism is to be operated so as to switch the state from the interlock state to the interlock release state and the position switching mechanism is to be operated so as to switch the position from the interlock position to the retraction position, as well as when the interlock switching mechanism is to be operated so as to switch the state from the interlock release state to the interlock state and the position switching mechanism is to be operated so as to switch the position from the retraction position to the interlock position.

Advantage of the Present Invention

With the overlock sewing machine having the above-described configuration, such an overlock sewing machine is capable of preventing the state thereof from switching to the interlock state or otherwise the interlock release state without the user's intention, and of preventing the position of the upper blade from switching to the interlock position or otherwise the retraction position without the user's intention.

DESCRIPTION OF THE PREFERRED EMBODIMENTS

Figure 1:
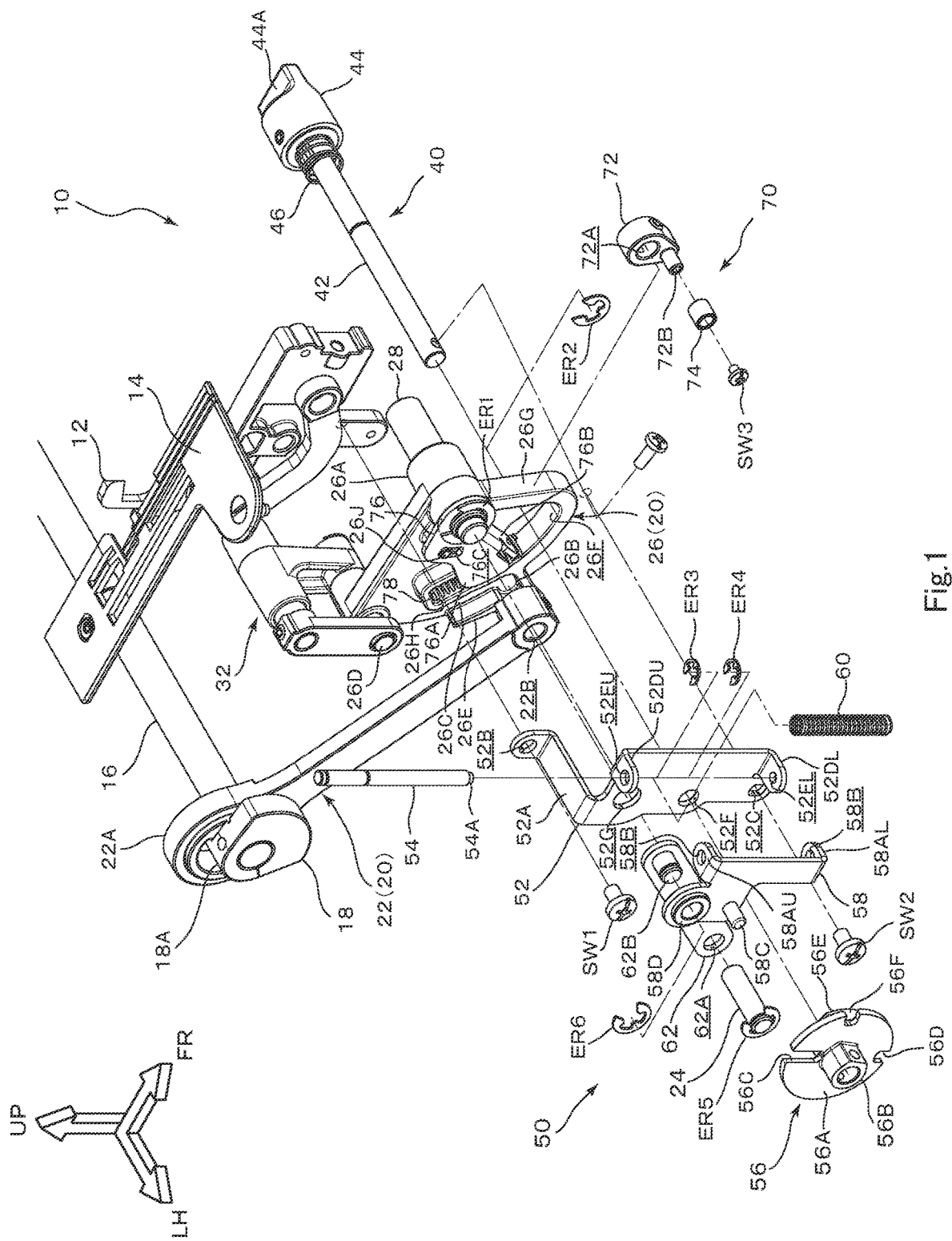
FIG. 1 is an exploded perspective view showing principal components of an overlock sewing machine according to the present embodiment as viewed from the diagonally left-front side.

Description will be made below regarding an overclock sewing machine 10 according to the present invention. It should be noted that, in the drawings shown as appropriate, the arrow UP indicates the upper side of the overlock sewing machine 10, the arrow FR indicates the front side thereof, and the arrow LH indicates the left side thereof (one side in the width direction). The directions used in the following description, i.e., the upper-lower direction, the front-back direction, and the left-right direction, represent the upper and lower, front and back, and left and right directions of the overlock sewing machine 10, unless otherwise noted.

Figure 2:
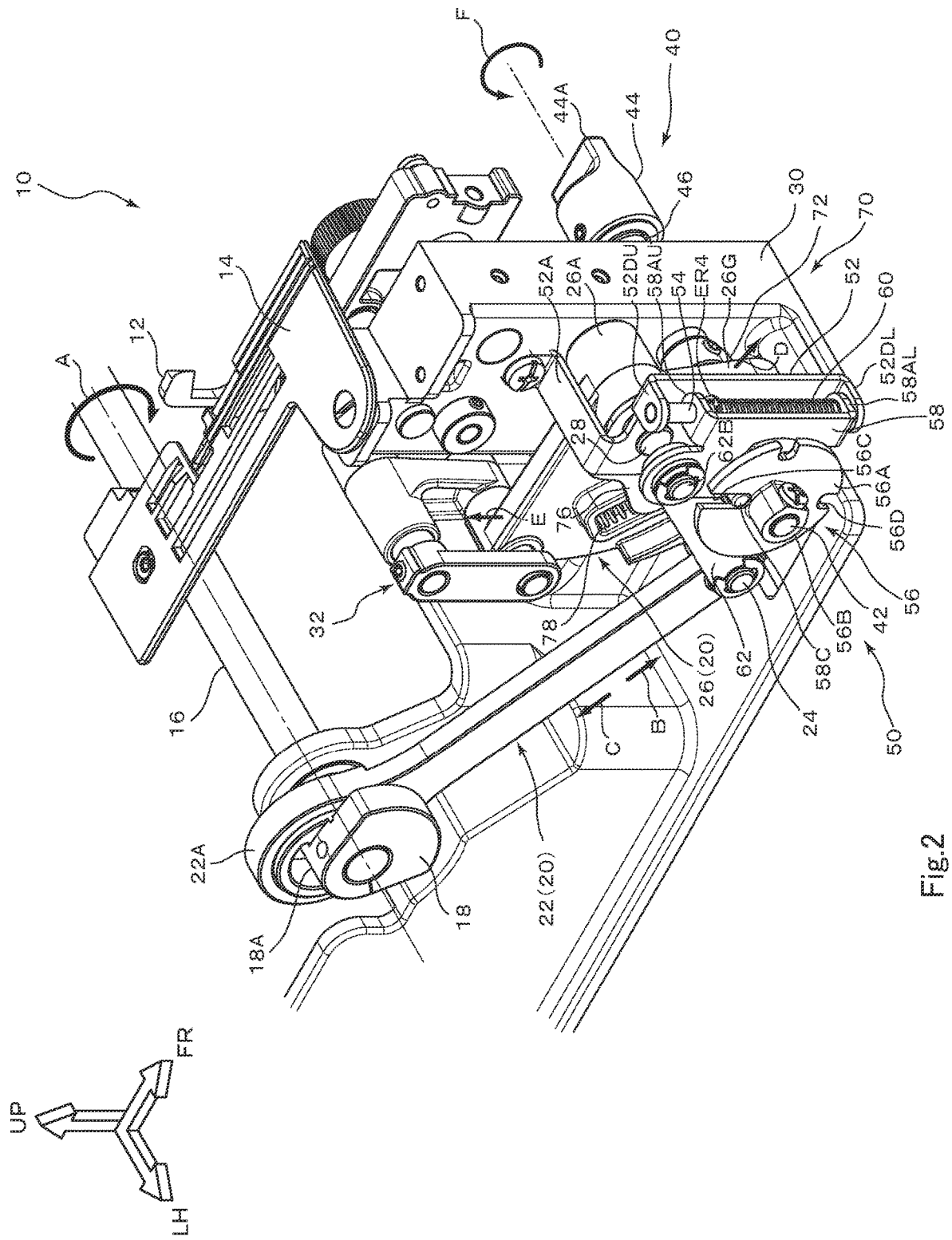
FIG. 2 is a perspective view showing principal components of the overlock sewing machine according to the present embodiment in the interlock state as viewed from the diagonally left-front side.

As shown in FIGS. 1 and 2, the overlock sewing machine is configured including: an upper blade 12; a driving mechanism 20 configured to transmit a rotational force of a main shaft 16 to the upper blade 12 so as to drive the upper blade 12; an interlock switching mechanism 50 configured to switch the operating state to an interlock state in which the upper blade 12 is operated together with the rotation of the main shaft 16 or otherwise an interlock release state in which the above-described interlock state is released; a position switching mechanism 70 configured to switch the position of the upper blade 12; and an operating mechanism 40 configured to operate the interlock switching mechanism and the position switching mechanism 70. Description will be made below regarding each component of the overlock sewing machine 10. It should be noted that description will be made assuming that the overlock sewing machine 10 is set to the interlock state, unless otherwise noted.

[Regarding the Upper Blade]

The upper blade 12 is arranged on the right side of a needle plate 14. The upper blade 12 is coupled to the main shaft 16 by the driving mechanism 20 and a link mechanism 32. The upper blade 12 is configured to be forced downward by a spring (not shown), and to be reciprocally moved in the upper-lower direction together with the rotation of the main shaft 16 (the position at which the upper blade 12 is moved together with the rotation of the main shaft 16 will be referred to as the "interlock position" hereafter). With such an arrangement, when the upper blade 12 is set to the interlock position, the upper blade 12 is moved in the upper-lower direction such that it is pressed in contact with a lower blade (not shown), thereby allowing a sewing target on the needle plate 14 to be cut. That is to say, the interlock position of the upper blade 12 represents a position in a predetermined range in which the upper blade 12 is driven in the upper-lower direction together with the rotation of the main shaft 16.

Furthermore, the upper blade 12 is configured such that it can be moved to a retraction position (the position of the upper blade 12 shown in FIGS. 7A and 7B) positioned further on the lower side than the interlock position. When the position switching mechanism 70 operates the upper blade 12 as described later, the position of the upper blade 12 is switched to the retraction position or otherwise the interlock position.

[Regarding the Driving Mechanism]

The driving mechanism 20 is configured including an upper blade rod 22 configured as a "rod" and a swing arm 26 configured as a "swing member".

[Regarding the Upper Blade Rod]

The upper blade rod 22 is coupled to the main shaft 16 by a blade cam 18 configured as an "eccentric cam". The upper blade rod 22 is configured such that it is swung by rotation of the main shaft 16. Specifically, the main shaft 16 is arranged with the left-right direction as its axial direction. Furthermore, the blade cam 18 is fixed to one end portion (left-end portion) of the main shaft 16 such that it can be rotated together with the main shaft 16 as a single unit. The blade cam 18 includes an eccentric cam portion 18A that is eccentric with respect to the axis of the main shaft 16. The eccentric cam portion 18A converts the rotation of the main shaft 16 into motion on a plane that is orthogonal to the axial direction of the main shaft 16. It should be noted that the other end portion (right-end portion) of the main shaft 16 is coupled to an unshown driving motor. When the driving motor drives the main shaft 16, the main shaft 16 is rotated around its axis.

The upper blade rod 22 is arranged such that it extends along a direction that is orthogonal to the axial direction of the main shaft 16. An approximately ring-shaped circular portion 22A is formed in one end portion of the upper blade rod 22. The eccentric cam portion 18A of the blade cam 18 described above is rotatably fitted into an internal space of the circular portion 22A. With this arrangement, when the main rod 16 is rotated around its axis (in the direction indicated by the arrow A shown in FIG. 2), the upper blade rod 22 is reciprocally swung in the arrow B direction and the arrow C direction shown in FIG. 2.

A fixing hole portion 22B is formed in the other end portion of the upper blade rod 22 in the form of a through hole such that it extends in the left-right direction. A rod pin 24 configured as a "fitting target portion" or a "fitting target shaft" is fitted into the fixing hole portion 22B, which fixes the rod pin 24 to the other end portion in the longitudinal direction of the upper blade rod 22. In a state in which the rod pin 24 is fixed to the upper blade rod 22, an end portion (right-end portion) of the rod pin 24 is arranged such that it protrudes from the upper blade rod 22 toward the right side. Furthermore, the end portion is fitted into a fitting groove 26B of the swing arm 26 described later. With this arrangement, the upper blade rod 22 is coupled to the swing arm 26 described later, which allows the planar motion of the blade cam 18 to be converted into swinging motion of the swing arm 26.

[Regarding the Swing Arm]

The swing arm 26 is arranged on the right side with respect to the other end portion of the upper blade rod 22. Furthermore, the swing arm 26 is configured in an approximately fan-plate shape with the left-right direction as its thickness direction. An approximately cylindrical bearing portion 26A configured with the left-right direction as its axial direction is monolithically formed in a base end portion (a portion that corresponds to the center of the fan-shaped structure) of the swing arm 26. The bearing portion 26A is configured such that it protrudes toward the right side from the swing arm 26. The arm support shaft 28 configured as a "support shaft" with the left-right direction as its axial direction is inserted into an internal space of the bearing portion 26A. In this state, the bearing portion 26A is rotatably supported by an arm support shaft 28. With this arrangement, the swing arm 26 is configured such that it can be reciprocally swung around the axis of the arm support shaft 28. In the following description, the direction indicated by the arrow D shown in FIG. 2 indicates the direction in which the swing arm 26 is moved forward in its reciprocal swinging operation. In contrast, the direction indicated by the arrow E indicates the direction in which the swing arm 26 is moved in reverse in its reciprocal swinging operation.

It should be noted that the arm support shaft 28 is arranged such that it protrudes toward the right side with respect to the bearing portion 26A. Furthermore, the base end portion of the arm support shaft 28 is fixed to a sewing machine housing 30 (not shown in FIG. 1). Moreover, a retaining ring ER1 is engaged with the end portion of the arm support shaft 28. The retaining ring ER1 is arranged adjacent to the left side of the shaft bearing portion 26A via a roller receiving plate 76 described later. With such an arrangement, the bearing portion 26A is arranged such that it is interposed between the sewing machine housing 30 and the retaining ring ER1. With this arrangement, the movement of the swing arm 26 in the left-right direction is restricted by the sewing machine housing 30 and the retaining ring ER1. Furthermore, the end portion of the arm support shaft 28 is supported by a holder 52 of the interlock switching mechanism 50 described later. The structure of the holder 52 will be described later.

Figure 7A:
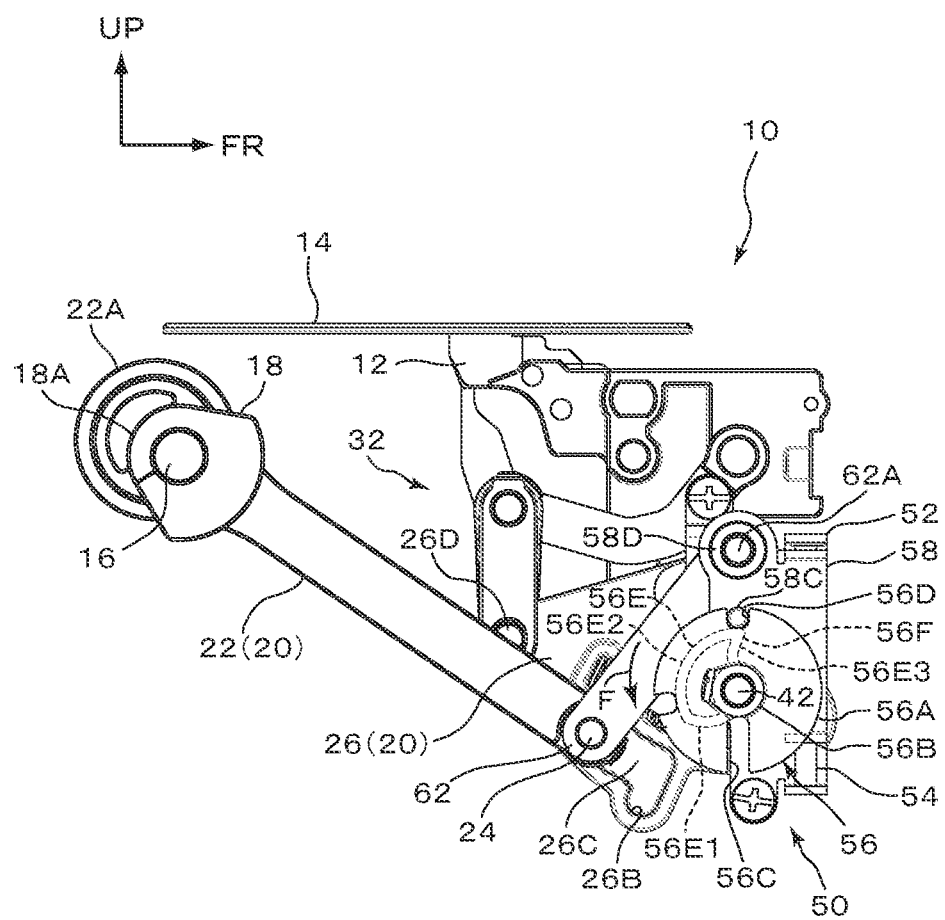
FIG. 7A is a side view as viewed from the left side showing the interlock switching mechanism when the operating shaft is turned from the state shown in FIG. 6A in the rotation operation direction and set to the interlock release state.
Figure 7B:
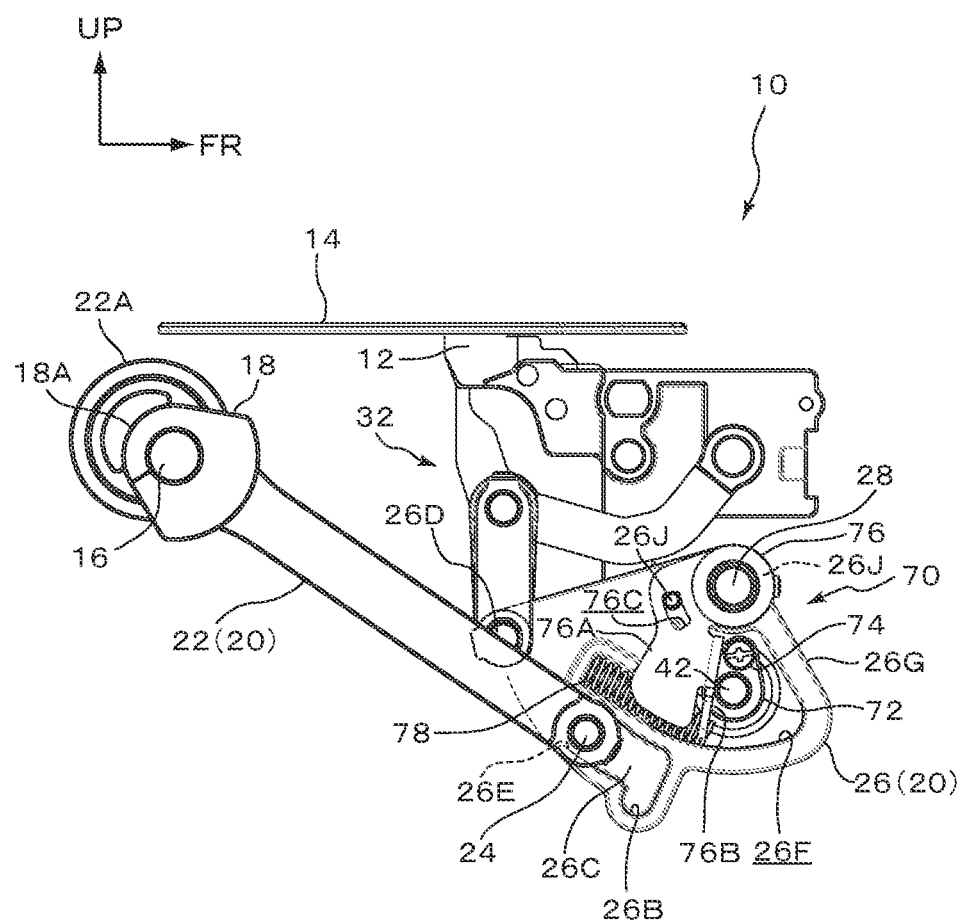
FIG. 7B is a side view as viewed from the left side showing the position switching mechanism in the state shown in FIG. 7A when the upper blade is switched to the retraction position.

As also shown in FIG. 7B, the fitting groove 26B configured as a "fitting portion" is formed in an intermediate portion of the end portion of the swing arm 26 (a curved portion having an approximately arc shape as viewed in a side view) such that it extends on one face (left-side face) in the thickness direction of the swing arm 26. The fitting groove 26B is configured in a recess structure with an opening facing the left side. Furthermore, the fitting groove 26B is configured in a groove structure with an opening facing the inner side of a radial direction of the swing arm 26 as viewed from the left side (i.e., on the arm support shaft 28 side). The fitting groove 26B is designed to have a groove width that is slightly larger than the diameter of the above-described rod pin 24. Furthermore, a communication groove 26C is formed in one face in the thickness direction of the swing arm 26, which is formed on the inner side of a radial direction of the swing arm 26 with respect to the fitting groove 26B. The communication groove 26C is configured in a recess structure with an opening that faces the left side such that it extends along the circumferential direction of the arm support shaft 28 (i.e., the swing direction of the swing arm 26). Furthermore, the communication groove 26C is configured such that its one end portion communicates with the fitting groove 26B, and such that the other end portion thereof has an opening that faces the reverse swing side of the swing arm 26. Moreover, the communication groove 26C is configured to have a groove width that is larger than the diameter of the above-described rod pin 24.

Furthermore, a connector portion 26D is provided to an end portion of the swing arm 26 on the reverse swing side thereof. The link mechanism 32 is connected to the connector portion 26D. This allows the swing arm 26 and the upper blade 12 to be connected via the link mechanism 32.

With such an arrangement, the end portion of the rod pin 24 of the upper blade rod 22 is detachably fitted into the fitting groove 26B. With this arrangement, the upper blade rod 22 and the swing arm 26 are connected. When the upper blade rod 22 is swung by rotating the main shaft 16, the swing arm 26 is reciprocally swung around the axis of the arm support shaft 28, which reciprocally moves the upper blade 12 in the upper-lower direction. That is to say, the state is set to the interlock state in which the upper blade set to the interlock position is driven in the upper-lower direction interlocked with the rotation of the main shaft 16 (see FIG. 2).

On the other hand, when the other end portion of the upper blade rod 22 in its longitudinal direction is displaced upward by the interlock switching mechanism 50 described later so as to detach the end portion of the rod pin 24 from the fitting groove 26B and to set the end portion of the rod pin 24 into the communication groove 26C, the fitting state between the rod pin 24 and the fitting groove 26B is released. In this state, the interlock state between the upper blade 12 and the main shaft 16 is released (the state shown in FIGS. 7A and 7B, which will be referred to as the "interlock release state" hereafter).

Furthermore, a portion of the swing arm 26 adjacent to the reverse swing side with respect to the fitting groove 26B is defined as a support portion 26E. At a predetermined timing at which the operating state is switched from the interlock release state to the interlock state by the interlock switching mechanism 50 described later, the support portion 26E is configured to support the rod pin 24 from the lower side. Detailed description thereof will be made later.

Furthermore, as sown in FIGS. 1 and 4B, a positioning hole 26F is formed as a through hole extending in the left-right direction in a forward-swing-side portion of the swing arm 25 in order to allow a roller 74 described later and a part of the roller receiving plate 76 to be arranged. The positioning hole 26F is arranged on the outer side of the bearing portion 26A in a radial direction, and is configured to have an approximately trapezoidal shape curved in the circumferential direction of the bearing portion 26A as viewed in a side view. With such an arrangement, a forward-swing-side end portion of the swing arm 26 is defined as a roller receiving portion 26G that forms the position switching mechanism 70 described later. Accordingly, the roller receiving portion 26G forms a part of the edge portion of the positioning hole 26F. The roller receiving portion 26G is configured such that it can be rotated together with the swing arm 26 as a single unit such that it extends in an approximately linear fashion along an approximately radial direction of the arm support shaft 28.

Furthermore, a spring housing portion 26H is formed on one face of the swing arm 26 in its thickness direction such that it is positioned on the reverse swing side of the swing arm 26 with respect to the positioning hole 26F, in order to allow a buffer spring 78 of the position switching mechanism 70 described later to be housed. The spring housing portion 26H is configured in a recessed structure with an opening that faces that faces the left side such that it extends in an approximately circumferential direction of the swing arm 26. Moreover, in the swing arm 26, a forward-swing-side end portion of the spring housing portion 26H is configured to have an opening that faces the positioning hole 26F side such that it communicates with an outer circumferential portion of the positioning hole 26F.

Furthermore, a retaining pin 26J is monolithically formed on one face of the swing arm 26 in its thickness direction such that it is arranged on the rear side of the arm support shaft 28. The retaining pin 26J is formed in an approximately cylindrical shape with the left-right direction as its axial direction such that it protrudes toward the left side from the swing arm 26.

[Regarding the Operating Mechanism]

As shown in FIGS. 1 through 3, the operating mechanism is configured including an operating shaft 42, an operating knob 44, and a force-applying spring 46 configured as a "shaft force-applying member".

[Regarding the Operating Shaft]

The operating shaft 42 is configured in a longitudinal round bar shape with the left-right direction as its axial direction. Furthermore, the operating shaft 42 is arranged on the front side of the upper blade rod 22 such that its intermediate portion in the longitudinal direction passes through the positioning hole 26F of the swing arm 26. Furthermore, a portion of the operating shaft 42 on one side (left side) in its longitudinal direction is supported by the holder 52 described later such that it can be rotated and can be slid in the axial direction. On the other hand, the other end portion (right end portion) of the operating shaft 42 is supported by the sewing machine housing 30 such that it can be rotated and can be slid in the axial direction. Furthermore, the operating shaft 42 is arranged such that the other end portion of the operating shaft 42 in the longitudinal direction protrudes toward the right side from the sewing machine housing 30. In the following description, the position of the operating shaft 42 in a non-operating state (position of the operating shaft 42 shown in FIG. 3A) is represented as an "operation restricted position", which will also be referred to as a "first position". In contrast, the position of the operating shaft 42 slid toward the left side from the operation restricted position (position of the operating shaft 42 shown in FIG. 3B) is represented as an "operation enabled position", which will also be referred to as a "second position".

Furthermore, a retaining ring ER2 is engaged with an intermediate portion of the operating shaft 42 in its longitudinal direction. When the operating shaft 42 is set to the operation restricted position, the retaining ring ER2 is pressed into contact with the sewing machine housing 30 from the left side. This restricts the slide of the operating shaft 42 toward the right side when it is set to the operation restricted position.

[Regarding the Operating Knob]

The operating knob 44 is configured in an approximately cylindrical shape having a bottom and an opening that faces the left side. The operating knob 44 is arranged on the same axis as the operating shaft 42. The other end portion of the operating shaft 42 is inserted from the left side into the interior of the operating knob 44 such that the operating knob 44 is fixed to the operating shaft 42 such that they can be rotated as a single unit. Furthermore, an approximately rectangular block-shaped knob portion 44A is monolithically formed in the bottom portion (right-end portion) of the operating knob 44. The knob portion 44A is configured such that it protrudes toward the right side from the operating knob 44 with the upper-lower direction as its thickness direction. This arrangement allows the user to hold the knob portion 44A and to rotate the operating knob 44 in the counterclockwise direction as viewed from the left side (which corresponds to the arrow F direction shown in FIG. 2, which will be referred to as a "rotation operation direction" hereafter), which rotates the operating shaft 42 together with the operating knob 44.

[Regarding the Force-Applying Spring]

The force-applying spring 46 is configured as a compression coil spring. The force-applying spring 46 is attached to a portion of the other end side of the operating shaft 42 such that it is arranged between the operating knob 44 and the sewing machine housing 30. In this state, the force-applying spring 46 comes to be in a compressive deformation state from its neutral state. Accordingly, the operating shaft 42 is forced toward the right side by the force-applying spring 46, and is held at the operation restricted position. With such an arrangement, when the user presses the knob portion 44A toward the left side against the force applied by the force-applying spring 46, the operating shaft 42 is slid from the operation restricted position to the operation enabled position.

[Regarding the Interlock Switching Mechanism]

As shown in FIGS. 1 through 3, the interlock switching mechanism 50 is configured including the holder 52, a guide shaft 54, a cam 56 configured as a "rotating member", a interlock switching plate 58 configured as an "interlock switching member", a return spring 60 configured as a "switching force-applying member", and an interlock switching arm 62 (which is a component that can be broadly regarded as a "coupling member").

[Regarding the Holder]

The holder 52 is configured as a plate-shaped member such that it extends in the upper-lower direction with the left-right direction as its thickness direction. A fixing tab 52A is formed in an upper end portion of a rear portion of the holder 52 such that it is bent toward the right side. The end portion of the fixing tab 52A is bent upward. An approximately circular fixing opening 52B is formed as a through hole in the end portion of the fixing tab 52A. With such an arrangement, a fixing screw SW1 is inserted into the fixing opening 52B from the left side such that the end portion of the fixing tab 52A is fixed to the sewing machine housing 30 by the fixing screw SW1. Furthermore, a fixing opening 52C is formed as a through hole in a lower end portion of the rear portion of the holder 52. The fixing hole 52C is formed in an approximately racing-track shape with the upper-lower direction as its longitudinal direction. With such an arrangement, a fixing screw SW2 is inserted into the fixing opening 52C from the left side. In this state, the holder 52 is fixed to the bottom wall portion of the sewing machine housing 30 by the fixing screw SW2.

A pair of upper and lower support tabs 52DU and 52DL are monolithically formed in a front portion of the holder 52 in order to support the guide shaft 54 described later. The pair of upper and lower support tabs 52DU and 52DL are bent toward the left side from the upper end portion and the lower end portion of the holder 52, respectively, such that they are arranged with the upper-lower direction as their thickness direction. Furthermore, an approximately circular support opening 52EU is formed as a through hole in the upper support tab 52DU. An approximately circular support opening 52EL is formed as a through hole in the lower support tab 52DL. The support openings 52EU and 52EL are arranged on the same axis. The support opening 52EU is designed to have an inner diameter that is larger than that of the support opening 52EL.

Furthermore, an approximately circular support opening 52F is formed as a through hole in an intermediate portion of the rear portion of the holder 52 in its upper-lower direction such that it is positioned on the upper side with respect to the fixing opening 52C. A portion on one side of the above-described operating shaft 52 in its axial direction is inserted into the support opening 52F such that it can be rotated and slid. Furthermore, an approximately circular support opening 52G is formed as a through hole in the holder 52 such that it is positioned on the upper side with respect to the support opening 52F. The end portion (left end portion) of the above-described arm support shaft 28 is inserted into and supported by the support opening 52G.

[Regarding the Guide Shaft]

The guide shaft 54 is mounted on the holder 52, and is configured to support the interlock switching plate 58 described later such that it can be moved in the upper-lower direction. Specifically, the guide shaft 54 is arranged with the upper-lower direction as its axial direction, and is inserted from the upper side into the support opening 52EU formed in the upper support tab 52DU of the holder 52. Furthermore, the lower end portion of the guide shaft 54 is defined as a shaft support portion 54A (see FIG. 1), and is designed to have a diameter that is smaller than that of the guide shaft 54. With this arrangement, a step portion is formed in the outer circumferential portion of the lower end portion of the guide shaft 54. With such an arrangement, the shaft support portion 54A is inserted from the upper side into the support opening 52EL formed in the lower support tab 52DL of the holder 52. The movement of the guide shaft 54 toward the lower side is restricted by the step portion thus formed in the guide shaft 54.

Furthermore, a retaining ring ER3 is engaged with the upper end portion of the guide shaft 54. The retaining ring ER3 is arranged adjacent to the lower side with respect to the upper support tab 52DU of the holder 52 (see FIG. 3). With this arrangement, the movement of the guide shaft 54 toward the upper side is restricted by the retaining ring ER3, thereby mounting the guide shaft 54 on the holder 52. Furthermore, a retaining ring ER4 is fixed to an intermediate portion of the guide shaft 54 in its axial direction (specifically, a portion closer to the upper side than the intermediate portion thereof in its axial direction) in order to engage the return spring 60 described later.

[Regarding the Cam]

The cam 56 is arranged on the left side with respect to the holder 52 (i.e., one side of the operating shaft 42 in its axial direction). The cam 56 includes a cam main body 56A. The cam main body 56A is configured in an approximately circular plate shape with the axial direction of the operating shaft 42 (i.e., left-right direction) as its thickness direction. A fixing cylinder portion 56B is monolithically formed in a central portion of the cam main body 56A. The fixing cylinder portion 56B is configured in an approximately cylindrical shape with the left-right direction as its axial direction such that it protrudes toward both sides in the thickness direction with respect to the cam main body 56A.

With such an arrangement, an end portion on one side of the operating shaft 42 in its axial direction is inserted from the right side into the interior of the fixing cylinder portion 56B. In this state, the fixing cylinder portion 56B is fixed to the operating shaft 42 by a fixing member such as a screw or the like. With this arrangement, the cam 56 is configured such that it can be rotated around the axis of the operating shaft 42 together with the operating shaft 42 as a single unit, and such that it can be slid in the axial direction of the operating shaft 42 together with the operating shaft 42 as a single unit. That is to say, the one side of the cam main body 56A in its circumferential direction matches the rotational operating direction of the operating shaft 42.

Figure 4A:
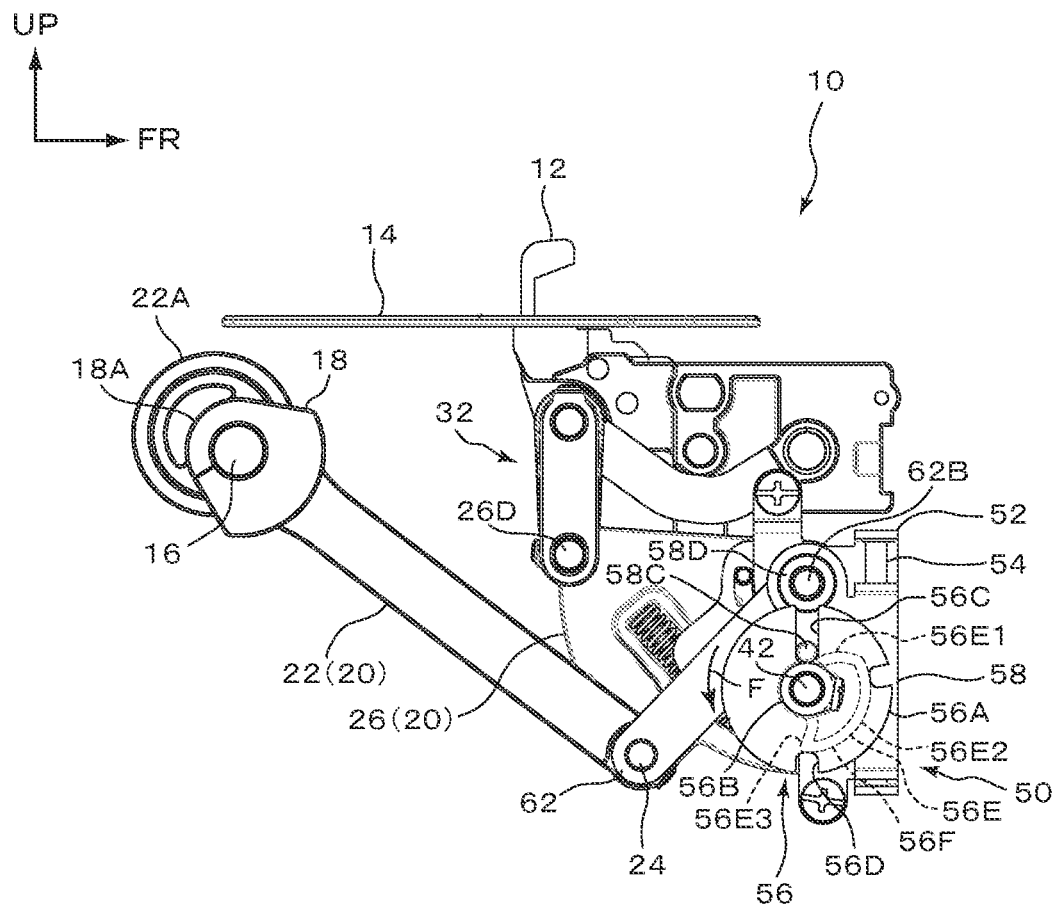
FIG. 4A is a side view as viewed from the left side showing an interlock switching mechanism in the state shown in FIG. 2.

Furthermore, as also shown in FIG. 4A, a first notch portion 56C is formed as a "first engagement target portion" in the cam main body 56A. The first notch portion 56C is formed in a groove structure with an opening that faces the outer side of the cam main body 56A in its radial direction as viewed in a side view. With such an arrangement, when the operating shaft 42 is not operated, the cam main body 54A is set such that the first notch portion 56C extends in the upper-lower direction and such that the opening of the first notch portion 56C faces the upper side (which is the position shown in FIGS. 2 and 4A; this position of the cam will be referred to as a "cam initial position" hereafter). Furthermore, the first notch portion 56C is designed to have a depth such that its bottom is adjacent to the outer face of the fixing cylinder portion 56B.

Furthermore, a second notch portion 56D configured as a "second engagement target portion" is formed in the cam main body 56A on a side that is opposite to the first notch portion 56C along the circumferential direction of the cam main body 56A. The second notch portion 56D is formed in a groove structure having an opening that faces the outer side in a radial direction of the cam main body 56A as viewed in a side view. The second notch portion 56D is arranged with an offset of approximately 180 degrees with respect to the first notch portion 56C along the circumferential direction of the cam main body 56A. Furthermore, the first notch portion 56C and the second notch portion 56D are each designed to have approximately the same width. Furthermore, the second notch portion 56D is designed to have a notch depth that is smaller than that of the first notch portion 56C. Specifically, the second notch portion 56D is designed to have a notch depth such that the bottom of the second notch portion 56D is positioned adjacent to a cam face 56F of a second cam portion 56E2 described later.

Furthermore, as shown in FIG. 4A, a cam portion 56E is monolithically formed on the right side face (face on the holder 52 side) of the cam main body 56A such that it is positioned at a front-side portion thereof (specifically, in a region of the cam main body 56A between the first notch portion 56C and the second notch portion 56D in the circumferential direction thereof). The outer face of the cam portion 56 is defined as the cam face 56F. The cam portion 56 is arranged such that, when the operating shaft is rotated in the rotational operation direction, an engagement pin 58C of the interlock switching plate 58 described later is slid on the cam face 56F. The cam portion 56E is configured in an approximately inverted C shape having an opening that faces the rear side as viewed in a side view. Both end portions of the cam portion 56E in its longitudinal direction are connected to the outer circumferential portion of the fixing cylinder portion 56B. Specifically, the cam portion 56E is configured including a first cam portion 56E1 configured as a portion on one side of the cam portion 56E in its longitudinal direction, a second cam portion 56E2 configured as an intermediate portion in the longitudinal direction of the cam portion 56E, and a third cam portion 56E3 configured as a portion on the other side of the cam portion 56E in its longitudinal direction.

The first cam portion 56E1 is arranged adjacent to the side that is opposite to the first notch portion 56C along the circumferential direction of the cam main body 56A. With such an arrangement, one end portion of the first cam portion 56E1 is connected to the fixing cylinder portion 56B of the cam 56. Furthermore, the first cam portion 56E1 is configured such that it extends from the fixing cylinder portion 56B toward the outer side in a radial direction of the cam main body 56A. Specifically, as viewed in a side view, the first cam portion 56E1 is configured such that, as the first cam portion 56E1 becomes closer to the outer side in a radial direction of the cam main body 56A, the first cam portion 56E1 further inclines and curves toward the other side in the circumferential direction of the cam main body 56A with a slight protrusion.

As viewed in a side view, the second cam portion 56E2 is configured such that it extends from the other end portion of the first cam portion 56E1 toward the other side of the cam main body 56A in its circumferential direction. Specifically, the second cam portion 56E2 is configured such that it is curved in an arc shape with the axis of the fixing cylinder portion 56B (i.e., the axis of the operating shaft 42) as the center. Furthermore, the second cam portion 56E2 is designed such that the distance between the axis of the operating shaft 42 and the cam face 56F of the second cam portion 56E2 is constant over the longitudinal direction of the second cam portion 56E2. Furthermore, as viewed in a side view, the second notch portion 56D is arranged adjacent to the outer side of the cam main body 56A in a radial direction with respect to the other end portion of the second cam portion 56E2.

The third cam portion 56E3 is configured such that it extends from the other end portion of the second cam portion 56E2 toward the inner side in a radial direction of the cam main body 56A. The third cam portion 56E3 is connected to the fixing cylinder portion 56B. Specifically, as viewed in a side view, the third cam portion 56E3 is configured such that, as the third cam portion 56E3 becomes closer to the inner side in a radial direction of the cam main body 56A, the third cam portion 56E3 is arranged with a slight slope toward the one side of the circumferential direction of the cam main body 56A.

[Regarding the Interlock Switching Plate]

As shown in FIGS. 1 and 2, the interlock switching plate 58 is arranged between the holder 52 and the cam 56 with the left-right direction as its thickness direction. Furthermore, as viewed in a side view, the interlock switching plate 58 is configured in an approximately inverted L shape having an opening as its diagonally lower-rear portion. The operating shaft 42 is arranged at this opening.

A pair of upper and lower guide tabs 58AU and 58AL are monolithically formed in the interlock switching plate 58. The upper-side guide tab 58AU is configured such that it is bent toward the right side from an upper-front end portion of the interlock switching plate 58. The lower-side guide tab 58AL is configured such that it is bent toward the right side from a lower-front end portion of the interlock switching plate 58. The pair of guide tabs 58AU and 58AL are arranged such that they face each other in the upper-lower direction with the upper-lower direction as their thickness direction. Guide openings 58B are formed as circular through holes in the pair of guide tabs 58AU and 58AL, respectively. Furthermore, the pair of upper and lower guide tabs 58AU and 58AL are designed such that the distance between them is smaller than the distance between the pair of upper and lower support tabs 52DU and 52DL described above. With such an arrangement, the pair of guide tabs 58AU and 58AL are arranged between the pair of support tabs 52DU and 52DL. Furthermore, the guide openings 58B are arranged on the same axis as the support openings 52EU and 52EL formed in the holder 52. The above-described guide shaft 54 is inserted into the guide openings 58B such that it can be relatively moved in the upper-lower direction. With this arrangement, the interlock switching plate 58 is mounted on the holder 52 such that it can be relatively moved in the upper-lower direction. Furthermore, in a state in which the interlock switching plate 58 is mounted on the holder 52, the retaining ring ER4 engaged with the intermediate portion of the guide shaft 54 in its longitudinal direction is arranged between the pair of guide tabs 58AU and 58AL (see FIG. 3).

Furthermore, the engagement pin 58C configured as an "engagement portion" is monolithically provided to a rear portion of the interlock switching plate 58. The engagement pin 58C is configured in an approximately cylindrical shape with the left-right direction as its axial direction. The engagement pin 58C is arranged such that it protrudes toward the left side from the interlock switching plate 58. The engagement pin 58C is designed to have a diameter that is slightly smaller than the width of each of the first notch portion 56C and the second notch portion 56D formed in the cam 56 described above. Specifically, the engagement pin 58C is configured such that it can be engaged with each of the first notch portion 56C and the second notch portion 56D.

Specifically, in a state in which the cam 56 (operating shaft 42) is set to the operation restricted position, the engagement pin 58C is inserted from the right side into the interior of the first notch portion 56C or otherwise the second notch portion 56D, which engages the engagement pin 58C with the first notch portion 56C or the second notch portion 56D along the circumferential direction of the cam 56 (operating shaft 42). In this state, the rotation of the cam 56 is restricted by the engagement pin 58C (i.e., interlock switching plate 58), which restricts the rotational operation for the operating shaft 42.

In contrast, in a state in which the cam 56 (operating shaft 42) is slid from the operation restricted position to the operation enabled position, the cam main body 56A of the cam 56 is moved toward the left side away from the engagement pin 58C, which releases the engagement state between the engagement pin 58C and the first notch portion 56C or otherwise the second notch portion 56D. With such an arrangement in this state, the rotation of the cam 56 is enabled, which enables the rotational operation for the operating shaft 42.

Furthermore, the engagement pin 58C is configured such that it can be pressed in contact with the outer circumferential face of the fixing cylinder portion 56B of the cam 56 and the cam face 56F. When the operating shaft 42 is not operated, the engagement pin 58C is set such that it comes in contact with the outer circumferential face of the fixing cylinder portion 56B and such that it is adjacent to the one side of the cam main body 56A in the circumferential direction of the cam main body 56A with respect to the cam portion 56E of the cam 56 (see FIG. 4A). With such an arrangement, when the cam 56 is rotated in the rotational operation direction for the operating shaft 42, the engagement pin 58C is slid on the cam face 56F. This displaces the interlock switching plate 58 toward the upper side while it is guided by the guide shaft 54.

Furthermore, the interlock switching plate 58 is provided with a bush 58D such that it is positioned on the upper side of the engagement pin 58C, in order to couple the interlock switching arm 62 described later.

[Regarding the Return Spring]

The return spring 60 is configured as a compression coil spring, and is mounted on the guide shaft 54.

Specifically, the upper end of the return spring 60 is engaged with the retaining ring ER4 provided to the guide shaft 54. The lower end of the return spring 60 is engaged with the lower guide tab 58AL of the interlock switching plate 58. The return spring 60 is mounted on the guide shaft 54 in a compressive deformation state from its neutral state (see FIGS. 2 and 3). With this arrangement, the interlock switching plate 58 is forced downward by the return spring 60. When the operating shaft 42 is not operated, the engagement pin 58C of the interlock switching plate 58 is pressed in contact with the outer circumferential face of the fixing cylinder portion 56B of the cam 56 by the force applied by the return spring 60.

[Regarding the Interlock Switching Arm]

As shown in FIGS. 1 and 2, the interlock switching arm is configured in an approximately longitudinal plate shape. The interlock switching arm 62 is arranged adjacent to and between the interlock switching plate 58 and the other end portion of the upper blade rod 22 with the left-right direction as its thickness direction. A circular coupling opening 62A is formed as a through hole in one end of the interlock switching arm 62. The base end portion (left-end portion) of the rod pin 24 described above is rotatably inserted into the coupling opening 62A. It should be noted that the one end portion of the interlock switching arm 62 is arranged such that it is interposed between the retaining ring ER5 engaged with the base end portion of the rod pin 24 and the other end portion of the upper blade rod 22 in the left-right direction. This restricts the movement of the interlock switching arm 62 in the left-right direction by the retaining ring ER5 and the upper blade rod 22.

On the other hand, a coupling pin 62B is provided to the other end portion of the interlock switching arm 62. The coupling pin 62B is configured in an approximately cylindrical shape with the left-right direction as its axial direction such that it protrudes from the interlock switching arm 62 toward the left side. Furthermore, the coupling pin 62B is arranged on the same axis as the arm support shaft 28 described above such that it is rotatably supported by the bush 58D of the interlock switching plate 58. With this arrangement, the interlock switching plate 58 and the rod pin 24 are coupled by the interlock switching arm 62.

When the interlock switching mechanism 50 is operated, the interlock switching plate 58 is raised, which displaces the interlock switching arm 62 upward. This releases the rod pin 24 away from the engagement groove 26B of the swing arm 26. Detailed description thereof will be made later. With this arrangement, this sets the operating state to the interlock release state in which the interlock state between the main shaft 16 and the upper blade 12 is released. With such an arrangement, when the interlock switching mechanism 50 is operated in the interlock release state, the interlock switching plate 58 is lowered, which displaces the interlock switching arm 62 toward the lower side. In this state, the rod pin 24 is engaged with the engagement groove 26B of the swing arm 26. With this arrangement in this state, the main shaft 16 and the upper blade 12 are returned to the interlock state. It should be noted that a retaining pin ER6 is engaged with the end portion of the coupling pin 62B, which allows the retaining ring ER6 to prevent the coupling pin 62B from detaching from the bush 58D.

[Regarding the Position Switching Mechanism]

Figure 4B:
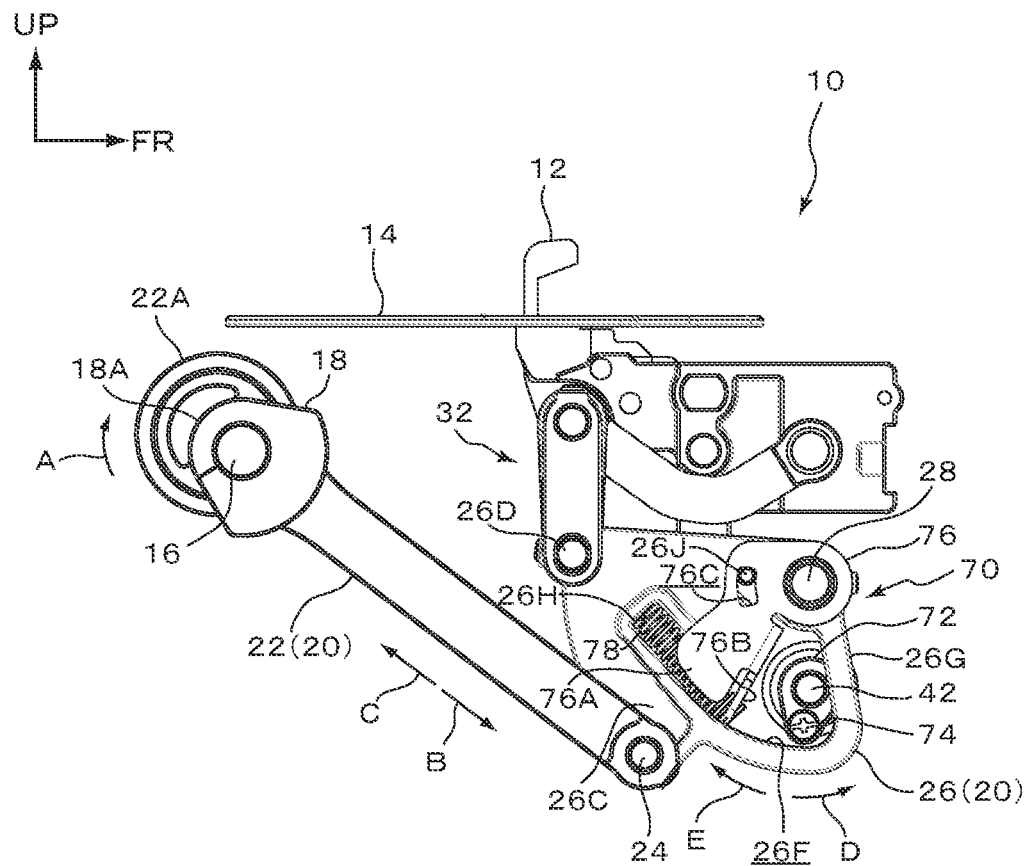
FIG. 4B is a side view as viewed from the left side showing a position switching mechanism in the state shown in FIG. 4A.

As shown in FIGS. 1, 2, and 4B, the position switching mechanism 70 is configured including the roller receiving portion 26G of the swing arm 26 described above, a position switching arm 72, a roller 74 configured as a "pressing portion", a roller receiving plate 76 configured as a "receiving member", and a buffer spring 78 configured as an "adjustment member". With such an arrangement, the roller receiving portion 26G corresponds to a "first switching portion" defined in the present invention. The roller receiving plate 76 and the buffer spring 78 correspond to a "second switching portion" defined in the present invention.

[Regarding the Position Switching Arm]

The position switching arm 72 is configured in an approximately wedge-shaped block shape with the left-right direction as its thickness direction. Specifically, the base end portion of the position switching arm 72 is configured in an approximately semicircular shape as viewed in a side view. Both side faces of the position switching arm 72 are configured to have a slope such that, as they become closer to the tip side, they approach each other. A circular fixing opening 72A is formed as a through hole in the base end portion of the position switching arm 72. An intermediate portion of the operating shaft 42 in its axial direction is inserted into the fixing opening 72A. In this state, the position switching arm 72 is fixed to the operating shaft 42 by a fixing member such as a screw or the like. With this arrangement, the position switching arm 72 is configured such that it can be rotated and slid together with the operating shaft 42 as a single unit.

A roller support shaft portion 72B is monolithically provided to the end portion of the position switching arm 72. The roller support shaft portion 72B is configured in an approximately cylindrical shape with the left-right direction as its axial direction. The roller support shaft portion 72B is arranged such that it protrudes toward the left side from the position switching arm 72. With such an arrangement, when the operating shaft 42 is not operated, the position switching arm 72 is set such that it is positioned on the right side of the swing arm 26, such that it extends downward from the operating shaft 42, and such that the roller support shaft portion 72B is positioned on the lower side with respect to the operating shaft 42.

[Regarding the Roller]

The roller 74 is configured in an approximately cylindrical shape with the left-right direction as its axial direction. The roller 74 is rotatably supported by the roller support shaft portion 72B of the position switching arm 72. With this arrangement, the roller 74 is configured such that it can be rotated around the axis of the operating shaft 42 and can be slid along the axial direction of the operating shaft 42 together with the rotating shaft 42 as a single unit. Furthermore, a fixing screw SW3 is screwed into the end portion of the roller support shaft portion 72B, which allows the fixing screw SW3 to prevent the roller 74 from detaching from the roller support shaft portion 72B. Furthermore, the roller 74 is arranged within the positioning hole 26F of the swing arm 26. With such an arrangement, when the operating shaft 42 is not operated, the roller 74 is positioned on the lower side with respect to the operating shaft 42. Furthermore, the roller 74 is set such that it is positioned (at the position of the roller 74 shown in FIG. 4B, which will be referred to as "roller initial position" hereafter) on the reverse swing side with respect to and away from the roller receiving portion 26G in order to prevent the occurrence of interference between the roller 74 and the roller receiving portion 26G of the swing arm 26 in a range in which the swing arm 26 is reciprocally swung according to the rotation of the main shaft 16.

On the other hand, when the operating shaft 42 is turned in the rotational operation direction so as to operate the position switching mechanism 70, the roller 74 is pressed into contact with the roller receiving portion 26G of the swing arm 26, which presses the roller receiving portion 26G toward the forward swing side. As a result, the swing arm 26 is swung toward the forward swing side. Detailed description thereof will be made later. In this state, the position of the upper blade 12 is switched to the retraction position from the interlock position.

[Regarding the Roller Receiving Plate]

The roller receiving plate 76 is arranged adjacent to the left side of the swing arm 26, and is arranged on the reverse swing side of the swing arm 26 with respect to the roller receiving portion 26G of the swing arm 26. The roller receiving plate 76 includes a plate main body 76A. The plate main body 76A is arranged with the left-right direction as its thickness direction, and is configured in an approximately reverse-L shape as viewed in a side view. With such an arrangement, the upper end portion of the plate main body 76A is rotatably supported by the end portion of the arm support shaft 28. Accordingly, the roller receiving plate 76 is configured such that it can be relatively rotated (moved) around the axis of the arm support shaft 28 with respect to the swing arm 26. It should be noted that the upper end portion of the roller receiving plate 76 is arranged such that it is interposed between the retaining ring ER1 engaged with the arm support shaft 28 and the bearing portion 26A of the swing arm 26. With this arrangement, the movement of the roller receiving plate 76 in the left-right direction is restricted by the retaining ring ER1 and the bearing portion 26A. Furthermore, the lower end portion of the plate main body 76A is arranged adjacent to the left side of the spring housing portion 26H of the swing arm 26, which covers a part of the opening of the spring housing portion 26H.

Furthermore, the roller receiving plate 76 includes a curved portion 76B. The curved portion 76B is configured such that it is bent at approximately a right angle toward the right side from the end portion of the plate main body 76A on the roller receiving portion 26G side. With this arrangement, the curved portion 76B is arranged within the interior of the positioning hole 26F of the swing arm 26. The curved portion 76B is configured such that it extends in a linear fashion along an approximately axial direction of the arm support shaft 28 as viewed in a side view. The roller 74 is arranged between the curved portion 76B and the roller receiving portion 26G.

Furthermore, an engagement opening 76C is formed as a through hole in the form of a "slot" in an upper end portion of the plate main body 76A on the rear side with respect to the arm support shaft 28. The engagement opening 76C is configured in a slot shape such that it is curved along the circumferential direction of the arm support shaft 28. The engagement pin 26J of the swing arm 26 is inserted into the engagement opening 76C such that it can be relatively moved.

[Regarding the Buffer Spring]

The buffer spring 78 is configured as a compression coil spring. The buffer spring 78 is housed within the spring housing portion 26H of the swing arm 26 in a state of being compressed and deformed from a neutral state such that it extends in an approximately circumferential direction of the swing arm 26. Specifically, one end of the buffer spring 78 is engaged with an inner circumferential face of the spring housing portion 26H. The other end of the buffer spring 78 is engaged with a lower end portion of the curved portion 76B of the roller receiving plate 76 in a state in which the other end portion of the buffer spring 78 protrudes toward the positioning hole 26F side of the swing arm 26 with respect to the spring housing portion 26H. With this arrangement, the roller receiving plate 76 is forced toward the forward swing side of the swing arm 26 by a force applied by the buffer spring 78, and one end portion of the engagement opening 76C of the roller receiving plate 76 is engaged with the retaining pin 26J of the swing arm 26 (which is a state shown in FIG. 4B; the position of the roller receiving plate 76 in this state will be referred to as a "hold position" hereafter). With such an arrangement, when the roller receiving plate 76 is set to the hold position, the curved portion 76B of the roller receiving plate 76 is positioned away from the reverse-swing-side edge portion of the positioning hole 26F of the swing arm 26 toward the forward swing side thereof. Furthermore, in this state, the roller 74 is set to a position away from the curved portion 76B toward the forward swing side in order to prevent the occurrence of interference between the roller 74 and the curved portion 76B in a range in which the swing arm 26 is reciprocally swung together with the rotation of the main shaft 16.

When the position switching mechanism 70 is operated according to the rotation of the operating shaft 42 in a state in which the upper blade 12 is set to the retraction position, the roller 74 is pressed in contact with the curved portion 76 of the roller receiving plate 76, which presses the buffer spring 78 via the curved portion 76B toward the reverse swing side of the swing arm 26. In this operation, the swing arm 26 is swung toward the reverse swing side, thereby switching the position of the upper blade 12 from the retraction position to the interlock position. Furthermore, in this operation, the roller receiving plate 76 is maintained at the hold position (a state in which there is no compressive deformation of the buffer spring, and no change in the relative position between the roller receiving plate 76 and the swing arm 26). In this state, the swing arm 26 is swung toward the reverse swing side. That is to say, the buffer spring 78 is designed to have a spring load that is larger than the force with which the swing arm 26 can be swung toward the reverse swing side.

Furthermore, with this arrangement, when the roller 74 presses the buffer spring 78 via the curved portion 76B with a predetermined load value or more, compressive deformation of the buffer spring 78 occurs (the buffer spring 78 is operated) such that the roller receiving plate 76 is turned from the hold position to the reverse swing side of the swing arm 26. Detailed description thereof will be made later. In other words, the roller receiving plate 76 is configured such that it is relatively turned toward the reverse swing side with respect to the swing arm 26 due to the compressive deformation of the buffer spring 78.

Operations and Effects

Next, description will be made regarding the operations and effects of the present embodiment with reference to each operation of the overlock sewing machine 10.

[Regarding the Operation of the Overlock Sewing Machine in the Interlock State]

The state shown in FIGS. 2 and 4 is the interlock state of the overlock sewing machine 10. In this state, the rod pin 24 of the upper blade rod 22 is fitted into an inner portion of a fitting groove 26B (not shown) such that the upper blade 12 is coupled to the main shaft 16 via the upper blade rod 22, the swing arm 26, and the link mechanism 32. Furthermore, in this state, the upper blade 12 is arranged at an interlock position.

Furthermore, in this state, the operating shaft 42 of the operating mechanism 40 is held at the operation restricted position by a force applied by the force-applying spring 46. The engagement pin 58C of the interlock switching plate 58 is inserted into within the first notch portion 56C of the cam 56. In this state, the first notch portion 56C of the cam 56 is engaged with the engagement pin 58C along the circumferential direction of the operating shaft 42, which restricts the rotational operation for the operating shaft 42. That is to say, this restricts the operations of the interlock switching mechanism 50 and the position switching mechanism 70.

With such an arrangement, when the main shaft 16 is rotated in the one rotational direction around its axis (direction indicated by the arrow A shown in FIGS. 2 and 4B), the blade cam 18 fixed to the main shaft 16 is rotated in the one rotational direction around the axis of the main shaft 16. In this operation, the eccentric cam portion 18A having an axis which is eccentric with respect to the axis of the main shaft 16 is driven in a cyclic manner on a plane that is orthogonal to the axis of the main shaft 16. The cyclic driving operation is applied to the circular portion 22A of the upper blade rod 22. With this arrangement, the upper blade rod 22 is swung in a reciprocal manner in the directions indicated by the arrows B and C shown in FIGS. 2 and 4B.

On the other hand, as described above, the rod pin 24 of the upper blade rod 22 is fitted into the fitting groove 26B of the swing arm 26. Accordingly, the swing arm 26 is reciprocally swung around the axis of the arm support shaft (see the arrows C and D shown in FIGS. 2 and 4B) according to the reciprocal swinging operation of the upper blade rod 22. With this arrangement, the upper blade 12 coupled to the swing arm 26 via the link mechanism 32 is reciprocally moved in the upper-lower direction, which allows the sewing target placed on the needle plate 14 to be cut.

Furthermore, in the position switching mechanism 70, the roller receiving plate 76 is held at the hold position by the buffer spring 78. Accordingly, when the swing arm 26 is reciprocally swung around the axis of the arm support shaft 28, the roller receiving plate 76 is reciprocally swung together with the swing arm 26 around the axis of the arm support shaft 28 in a state in which the roller receiving plate 76 is maintained at the hold position. Furthermore, the swing arm 26 is reciprocally swung in a state in which the roller receiving portion 26G of the swing arm 26 and the curved portion 76B of the roller receiving plate 76 do not come in contact with the roller 74. This allows the swing arm 26 to be reciprocally swung without the occurrence of interference in the reciprocal swinging operation of the swing arm 26 due to the position switching mechanism 70.

Furthermore, in the interlock switching mechanism 50, one end portion (coupling opening 62A) of the interlock switching arm 62 is rotatably coupled to the rod pin 24 of the upper blade rod 22. The other end portion (coupling pin 62B) of the interlock switching arm 62 is rotatably coupled to the bush 58D of the interlock switching plate 58. Furthermore, the coupling pin 62B is arranged on the same axis as the arm support shaft 28, which functions as the center around which the swing arm 26 is to be swung. Accordingly, when the upper blade rod 22 is reciprocally swung, the interlock switching plate 58 is reciprocally swung around the axis of the coupling pin 62B. With this arrangement, the swinging of the upper blade rod 22 is not transmitted to the interlock switching plate 58. In this state, the interlock switching plate 58 is not displaced upward. This allows the swing arm 26 to be reciprocally swung without the occurrence of interference in the reciprocal swinging operation of the swing arm 26 due to the interlock switching mechanism 50.

[Operation in which the Overlock Sewing Machine is Switched from the Interlock State to the Interlock Release State and the Position of the Upper Blade is Switched from the Interlock Position to the Retraction Position]

When the overlock sewing machine 10 is switched from the interlock state to the interlock release state and the position of the upper blade 12 is switched from the interlock position to the retraction position, first, the operating shaft 42 is set to the rotational operation enabled state. Subsequently, the interlock switching mechanism 50 and the position switching mechanism 70 are operated by the operating shaft 42.

Figure 3A:
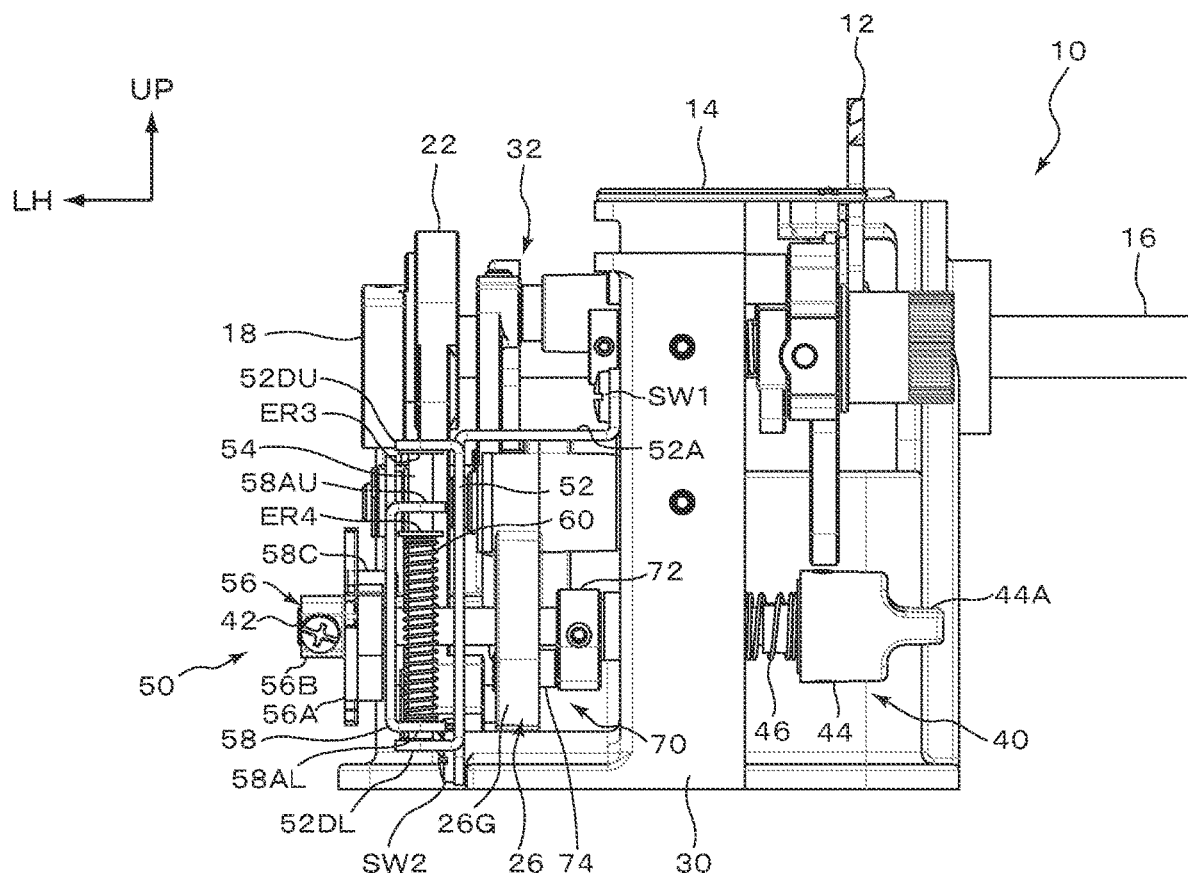
FIG. 3A is a front view showing a state in which an operating shaft is set to the operation restricted position shown in FIG. 2 as viewed from the front.
Figure 3B:
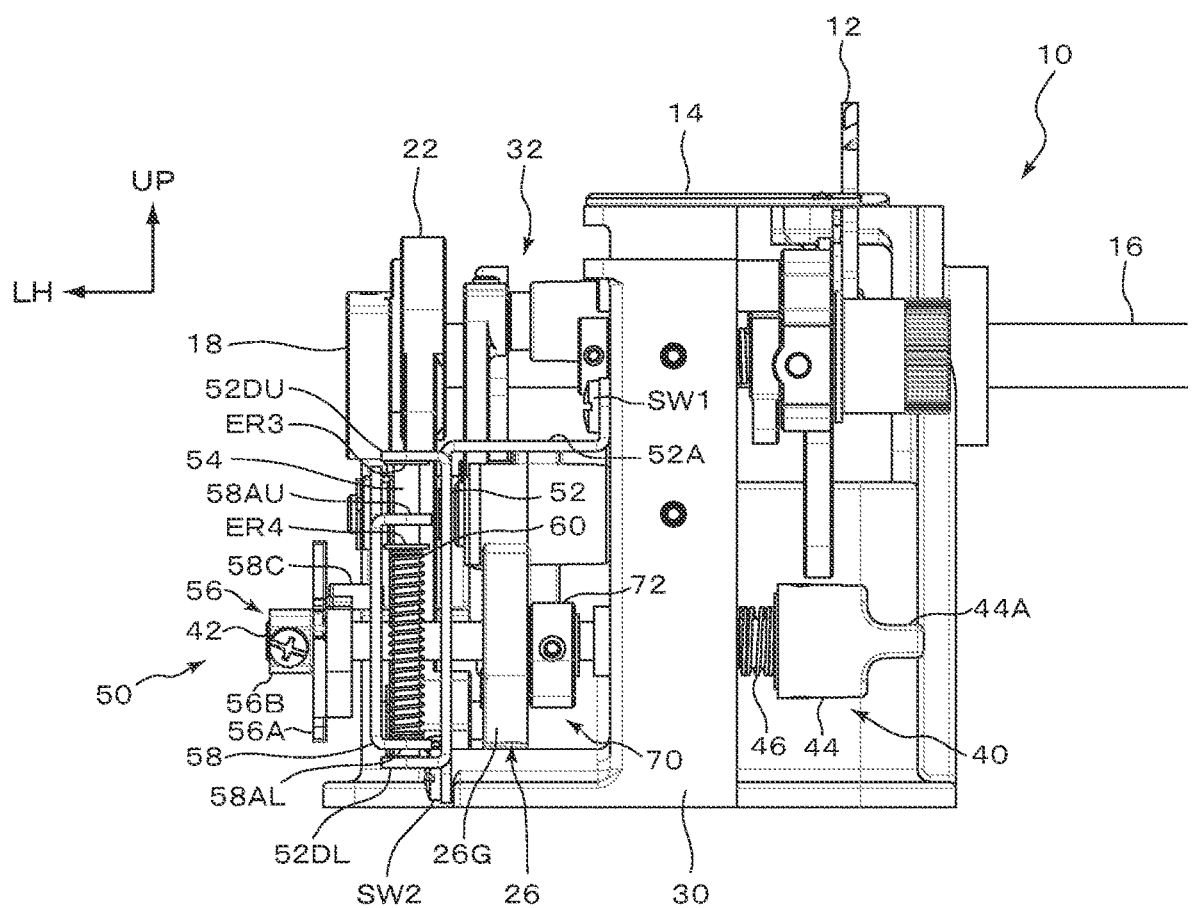
FIG. 3B is a front view showing a state in which the operating shaft is slid from the state shown in FIG. 3A to an operation enabled position.

That is to say, the user holds the knob portion 44A of the operating knob 44 in the state shown in FIG. 3A, and presses the operating knob 44 toward the left side against the force applied by the force-applying spring 46. In this operation, the operating shaft 42 is slid toward the left side from the operation restricted position, and is set to the operation enabled position shown in FIG. 3B. Furthermore, when the operating shaft 42 is slid from the operation restricted position to the operation enabled position, the cam 56 fixed to the operating shaft 42 is also slid toward the left side. Accordingly, the cam main body 56A of the cam 56 is displaced toward the left side away from the engagement pin 58C of the interlock switching plate 58, whereby the engagement pin 58C separates from the first notch portion 56C of the cam 56. In this state, the engagement state between the engagement pin 58C and the first notch portion 56C is released, which enables the rotational operation for the operating shaft 42.

Next, description will be made with reference to FIGS. 4 through 7 regarding a procedure for operating the interlock switching mechanism 50 and the position switching mechanism 70 by turning the operating knob 44 (operating shaft 42) in a state in which the rotational operation for the operating shaft 42 is enabled. It should be noted that, in FIGS. 4 through 7, the left-side and right-side drawings show the operating shaft 42 at the same rotational phase. In the right-side drawings, members such as the interlock switching plate 58, the holder 52, the guide shaft 54, the interlock switching arm 62, etc. are not shown for convenience.

FIG. 4 shows a state before the operating shaft 42 is rotationally operated. That is to say, FIG. 4 shows a state before the interlock switching mechanism 50 and the position switching mechanism 70 are operated. In this stage, the overlock sewing machine 10 is set to the interlock state, and the upper blade 12 is set to the interlock position.

As shown in FIG. 4A, in the interlock switching mechanism 50, the interlock switching plate 58 is forced downward by the return spring 60. In this state, the engagement pin 58C of the interlock switching plate 58 is pressed in contact with the outer circumferential face of the fixing cylinder portion 56B of the cam 56, and is positioned adjacent to a portion of the cam portion 56E positioned on the one side of the cam main body 56A along its circumferential direction.

On the other hand, as shown in FIG. 4B, in the position switching mechanism 70, the roller 74 is positioned within the positioning hole 26F of the swing arm 26, and is positioned on the lower side with respect to the operating shaft 42. Furthermore, the roller 74 is set to a position away from the roller receiving portion 26G of the swing arm 26 and the curved portion 76B of the roller receiving plate 76.

Subsequently, as shown in FIG. 5, the operating knob 44 is turned so as to turn the operating shaft 42 in the rotational operation direction (direction indicated by the arrow F in FIG. 4A). It should be noted that FIG. 5 shows a state after the operating shaft 42 is slightly turned in the rotational operation direction from the state shown in FIG. 4.

Figure 5A:
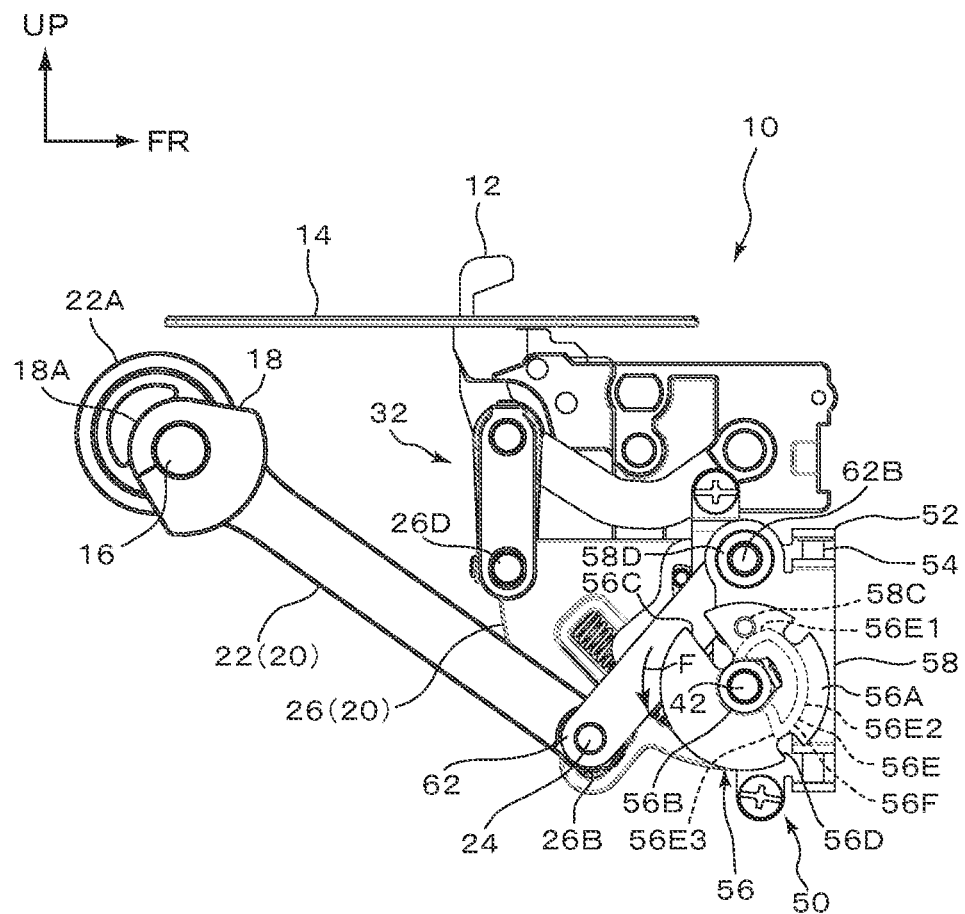
FIG. 5A is a side view as viewed from the left side showing the interlock switching mechanism when the operating shaft is turned from the state shown in FIG. 4A in the rotational operation direction.

As shown in FIG. 5A, in the interlock switching mechanism 50 in this state, the cam 56 is turned in the rotational operation direction together with the operating shaft 42. In this operation, the cam face 56F of the first cam portion 56E1 of the cam 56 comes in contact with the engagement pin 58C of the interlock switching plate 58, and the engagement pin 58C is displaced upward while it is slid on the cam face 56F of the first cam portion 56E1. Accordingly, the interlock switching plate 58 is raised against the force applied by the return spring 60. At the same time, the interlock switching plate 58 is relatively moved upward with respect to the holder 52 while it is guided by the guide shaft 54. With this arrangement, the interlock switching arm 62 coupled to the interlock switching plate 58 by the coupling pin 62B is displaced upward together with the interlock switching plate 58.

Furthermore, the rod pin 24 is coupled to one end portion of the interlock switching arm 62. Accordingly, the rod pin 24 is also displaced upward according to the upward displacement of the interlock switching arm 62. In this operation, the rod pin 24 is displaced such that it is detached from the fitting groove 26B of the swing arm 26. It should be noted that FIG. 5 shows a state in which the rod pin 24 has not completely detached from the fitting groove 26B.

Figure 5B:
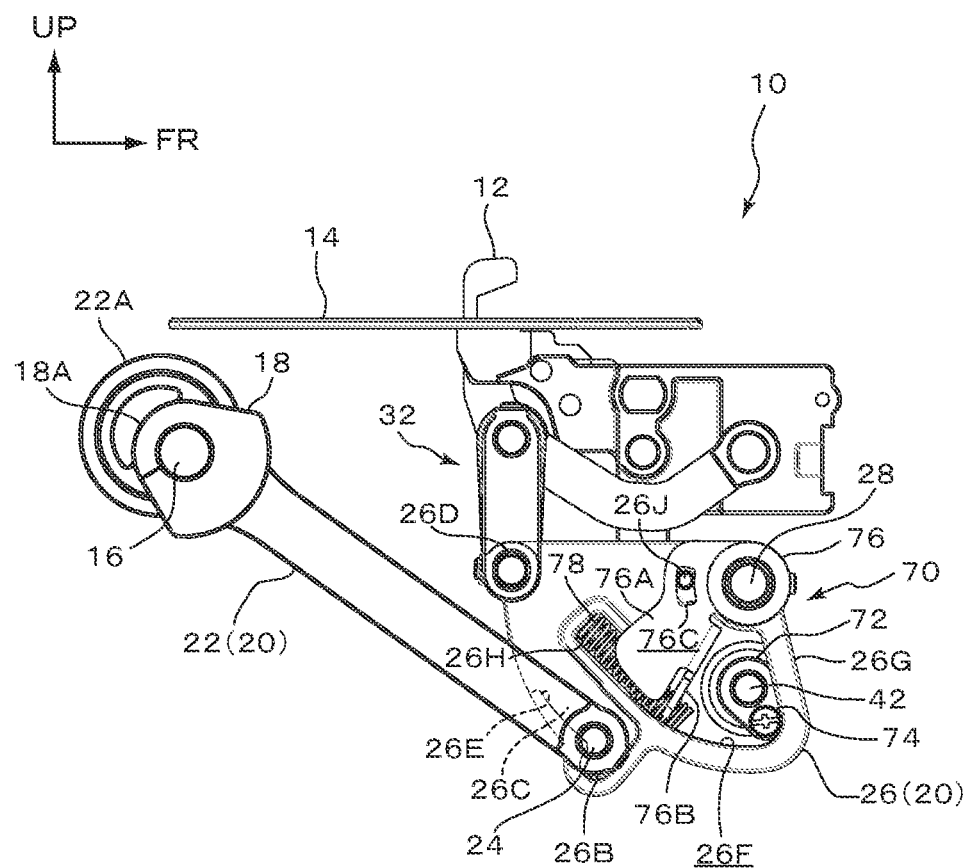
FIG. 5B is a side view as viewed from the left side showing the position switching mechanism in the state shown in FIG. 5A.

On the other hand, as shown in FIG. 5B, in the position switching mechanism 70, the position switching arm 72 is turned according to the rotation of the operating shaft 42 in the rotational operating direction. In addition, the roller 74 provided to the position switching arm 72 is turned in the rotational operation direction around the axis of the operating shaft 42. In this operation, the roller 74 is displaced from the roller initial position toward a position diagonally upward toward the front side such that it approaches the roller receiving portion 26G of the swing arm 26. It should be noted that FIG. 5B shows a state before the roller 74 has not come in contact with the roller receiving portion 26G.

Subsequently, as shown in FIG. 6, the operating knob 44 is turned so as to further turn the operating shaft 42 in the rotational operation direction from the state shown in FIG. 5.

Figure 6A:
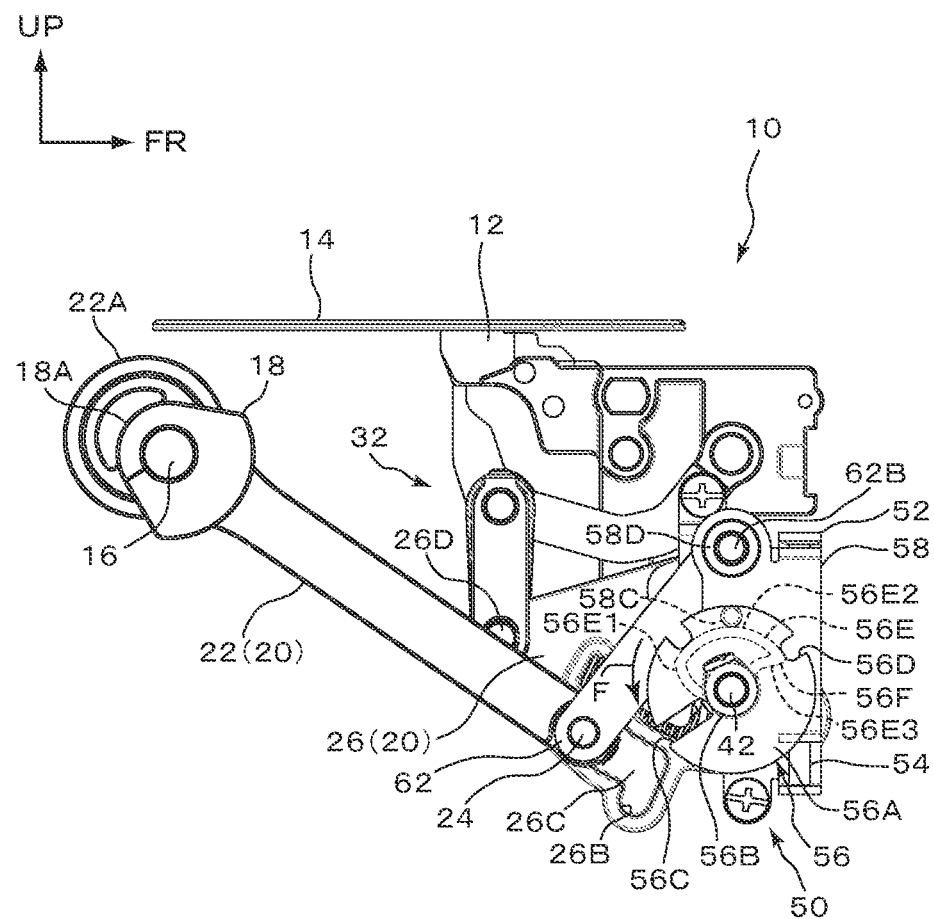
FIG. 6A is a side view as viewed from the left side showing the interlock switching mechanism when the operating shaft is turned from the state shown in FIG. 5A in the rotational operation direction.

As shown in FIG. 6A, with the interlock switching mechanism 50 in this state, the engagement pin 58C of the interlock switching plate 58 is displaced from the first cam portion 56E1 of the cam 56 to the second cam portion 56E2 thereof. Accordingly, the engagement pin 58C (interlock switching plate 58) is further displaced upward as compared with the position shown in FIG. 5. As a result, the rod pin coupled to the interlock switching plate 58 via the interlock switching arm 62 is completely detached from (no longer in contact with) the fitting groove 26B of the swing arm 26, and is positioned within the communicating groove 26C of the swing arm 26. In this operation, the interlock state between the upper blade rod 22 and the swing arm 26 is released, thereby switching the operation state to the interlock release state in which the interlock state between the main shaft 16 and the upper blade 12 is released.

It should be noted that, in the state shown in FIG. 6A, the engagement pin 58C of the interlock switching plate 58 comes in contact with an intermediate portion of the cam face 56F of the second cam portion 56E2. Furthermore, the second cam portion 56E2 is designed such that the distance between the axis of the swing arm 26 and the cam face 56F is set to be constant over the longitudinal direction of the second cam portion 56E2. Accordingly, even in the state shown in FIG. 6A, the interlock release state is maintained between the main shaft 16 and the upper blade 12.

Figure 6B:
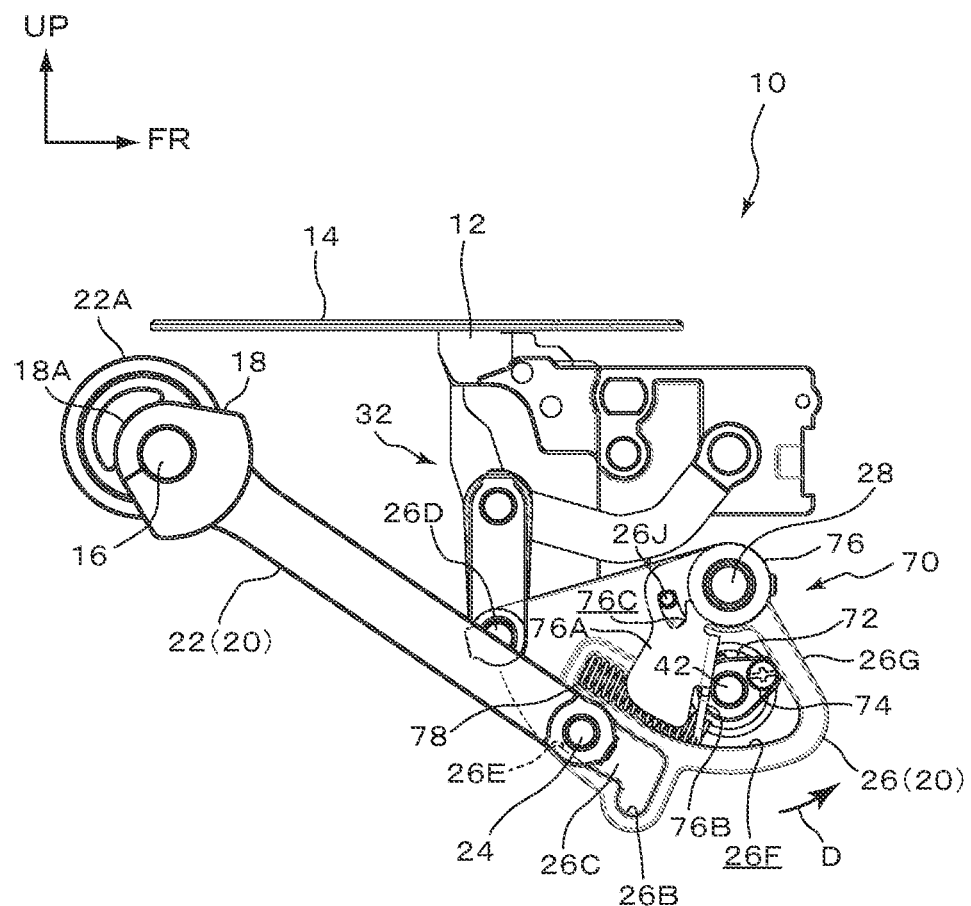
FIG. 6B is a side view as viewed from the left side showing the position switching mechanism in the state shown in FIG. 6A.

On the other hand, as shown in FIG. 6B, in the position switching mechanism 70, after the operation state is switched to the interlock release state (i.e., after the rod pin 24 is detached from the fitting groove 26B of the swing arm 26), the roller 74 is pressed in contact with the roller receiving portion 26G of the swing arm 26, which presses the roller receiving portion 26G toward the forward-swing side of the swing arm 26 (the side indicated by the arrow D direction in FIG. 6B). In this operation, rotational force is applied to the roller receiving portion 26G, which swings the roller receiving portion 26G and the swing arm 26 toward the forward swing side, and displaces the connector portion 26D of the swing arm 26 downward. Accordingly, the upper blade 12 coupled to the connector portion 26D via the link mechanism 32 is displaced downward from the interlock position.

Furthermore, in the state shown in FIG. 6B, the roller is positioned diagonally upward toward the front side with respect to the operating shaft 42. When the roller 74 is set to this position, the roller receiving portion 26G and the swing arm 26 are set by the roller 74 to the maximum swing position on the forward-swing side (this position of the swing arm 26 will be referred to as a "swing reverse position" hereafter). In this state, the upper blade 12 coupled to the swing arm 26 via the link mechanism 32 is displaced to the lowest side with respect to the interlock position such that it is set to the retraction position. In this operation as described above, the position of the upper blade 12 is switched by the position switching mechanism 70 from the interlock position to the retraction position.

It should be noted that, in the state shown in FIG. 6, the swing arm 26 is swung further toward the forward-swing side than the state shown in FIG. 5. Accordingly, the swing arm 26 is relatively displaced toward the forward-swing side with respect to the rod pin 24. As a result, the rod pin 24 supported by the interlock switching arm 62 is positioned within the communicating groove 26C.

Subsequently, as shown in FIG. 7, the operating knob 44 is turned so as to further turn the operating shaft 42 from the state shown in FIG. 6 in the rotational operating direction. Specifically, the operating shaft 42 is turned by an approximately 180 degrees from the position that corresponds to the state in which the operating shaft 42 is not operated. In this stage, the rotational operation for the operating shaft 42 ends.

As shown in FIG. 7A, in the interlock switching mechanism 50 in this state, the engagement pin 58C of the interlock switching plate 58 comes in contact with the cam face 56F of the other end portion of the second cam portion 56E2 formed in the cam 56. With such an arrangement, as described above, the second cam portion 56E2 is designed such that the distance between the axis of the operating shaft 42 and the cam face 56F is set to be constant over the longitudinal direction of the second cam portion 56E2. Accordingly, in the overlock sewing machine 10, the interlock release state is maintained between the main shaft 16 and the upper blade 12.

On the other hand, as shown in FIG. 7B, in the position switching mechanism 70, the roller 74 of the position switching arm 72 is set to a position on the upper side with respect to the operating shaft 42. When the roller 74 is set to this position, the roller 74 is displaced away from the roller receiving portion 26G of the swing arm 26, and is set to a position between the roller receiving portion 26G and the roller receiving plate 76 such that it comes in contact with neither the roller receiving portion 26G nor the roller receiving plate 76. That is to say, in this state, the roller 74 is set such that it presses neither the roller receiving portion 26G nor the roller receiving plate 76. Accordingly, in this state, the rotational force that can turn the swing arm 26 is applied to neither the roller receiving portion 26G nor the roller receiving plate 76. As a result, the swing arm 26 is maintained at the swing reverse position in a state in which the upper blade 12 is set to the retraction position.

Furthermore, in this state, as shown in FIG. 7A, as viewed in a side view, the engagement pin 58C of the interlock switching plate 58 is set to a position that overlaps the second notch portion 56D of the cam 56. Accordingly, in this state, this arrangement enables the cam main body 56A (i.e., operating shaft 42) to be slid (moved) toward the right side. In this operation, in the operating mechanism 40, the operating shaft 42 is slid toward the right side from the operation enabled position by the force applied by the force-applying spring 46, thereby setting the operating shaft 42 to the operation restricted position. In this stage, the cam 56 is slid toward the right side together with the operating shaft 42. As a result, the engagement pin 58C of the interlock switching plate 58 is inserted into the interior of the second notch portion 56D of the cam 56. In this operation, the second notch portion 56D of the cam 56 and the engagement pin 58C are engaged again with each other at a position along the circumferential direction of the operating shaft 42. Accordingly, when the rotational operation for the operating shaft 42 is completed, the operating state is returned again to a state in which the rotational operation for the operating mechanism 40 is restricted.

[Operation for Switching the Overlock Sewing Machine from the Interlock Release State to the Interlock State and Switching the Position of the Upper Blade from the Retraction Position to the Interlock Position]

When the overlock sewing machine 10 is to be switched from the interlock release state to the interlock state, and the position of the upper blade 12 is to be switched from the retraction position to the interlock position, the rotational operation for the operating shaft 42 is enabled again, and the interlock switching mechanism 50 and the position switching mechanism 70 are switched to the operation enabled state.

That is to say, in the state shown in FIG. 3A as described above, the user holds the operating knob 44 (knob portion 44A thereof), and presses the operating knob 44 toward the left side against the force applied by the force-applying spring 46. In this operation, the operating shaft 42 and the cam 56 are slid toward the left side from the operation restricted position, and are set to the operation enabled position shown in FIG. 3B. Accordingly, the cam main body 56A of the cam 56 is displaced toward the left side away from the engagement pin 58C of the interlock switching plate 58, which detaches the engagement pin 58C from the second notch portion 56D of the cam 56. In this operation, the engagement state between the engagement pin 58C and the second notch portion 56D is released, thereby enabling the rotation of the operating shaft 42 in the rotational operation direction.

Figure 8A:
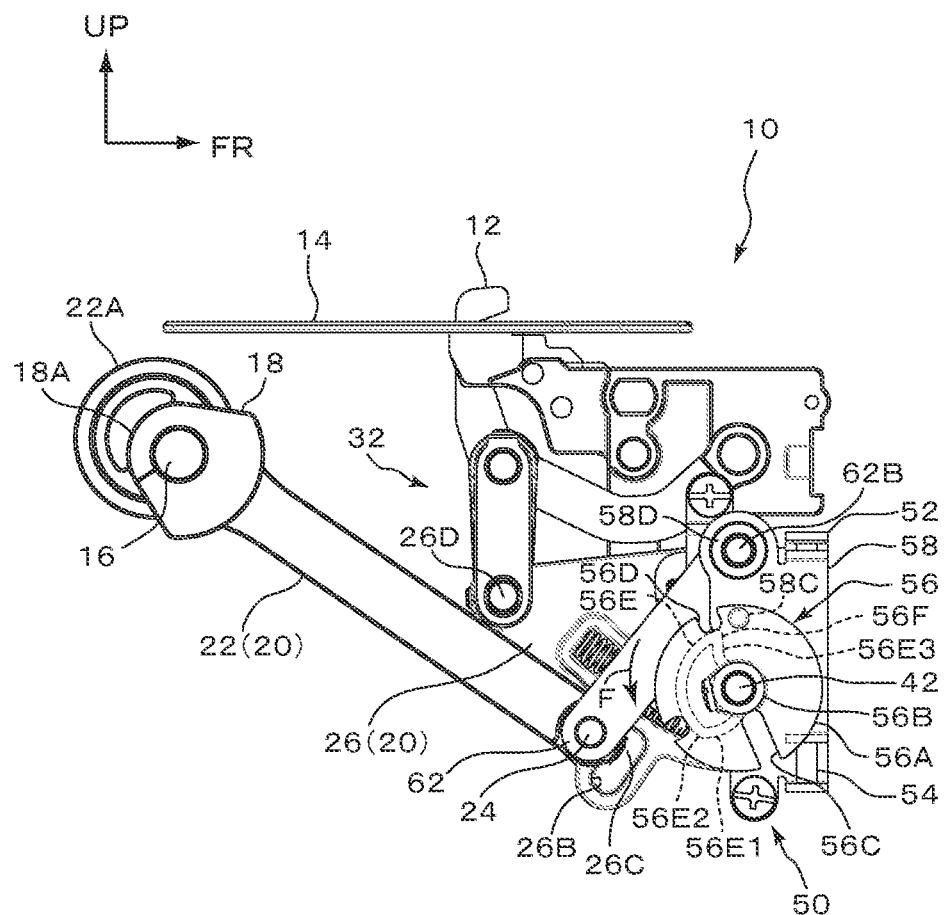
FIG. 8A is a side view as viewed from the left side showing the interlock switching mechanism when the operating shaft is turned from the state shown in FIG. 7A in the rotational operation direction.
Figure 9A:
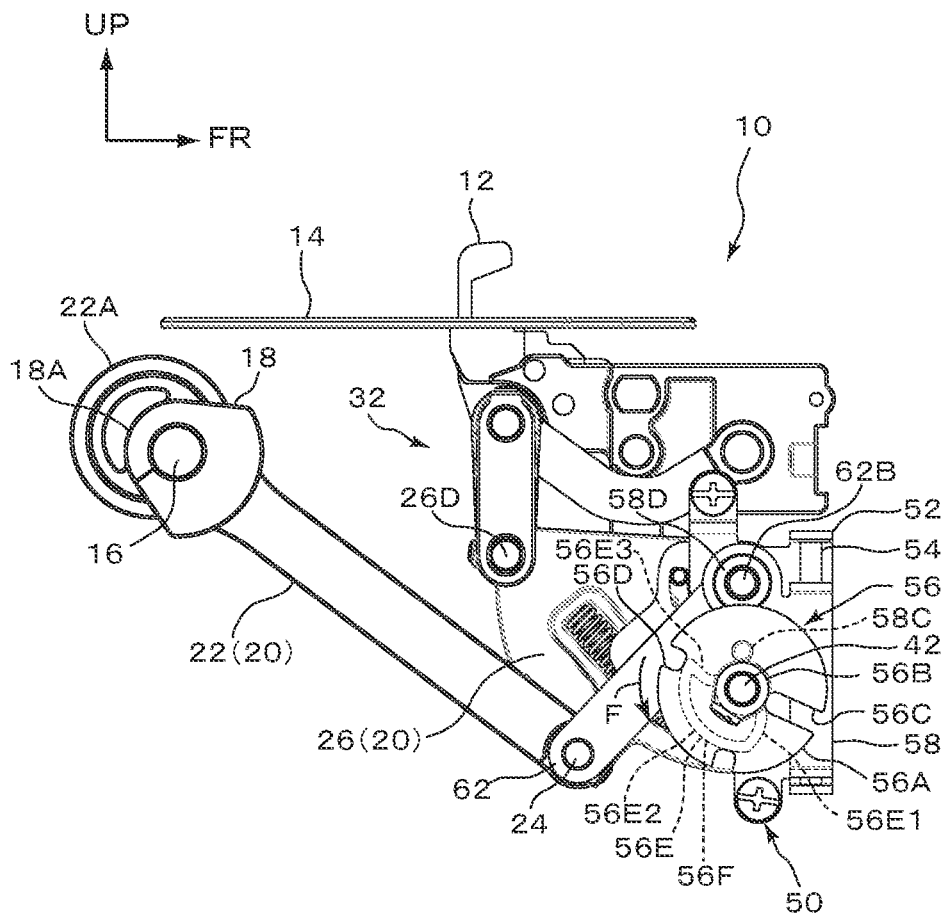
FIG. 9A is a side view as viewed from the left side showing the interlock switching mechanism when the operating shaft is turned from the state shown in FIG. 8A in the rotational operation direction and set to the interlock state.
Figure 9B:
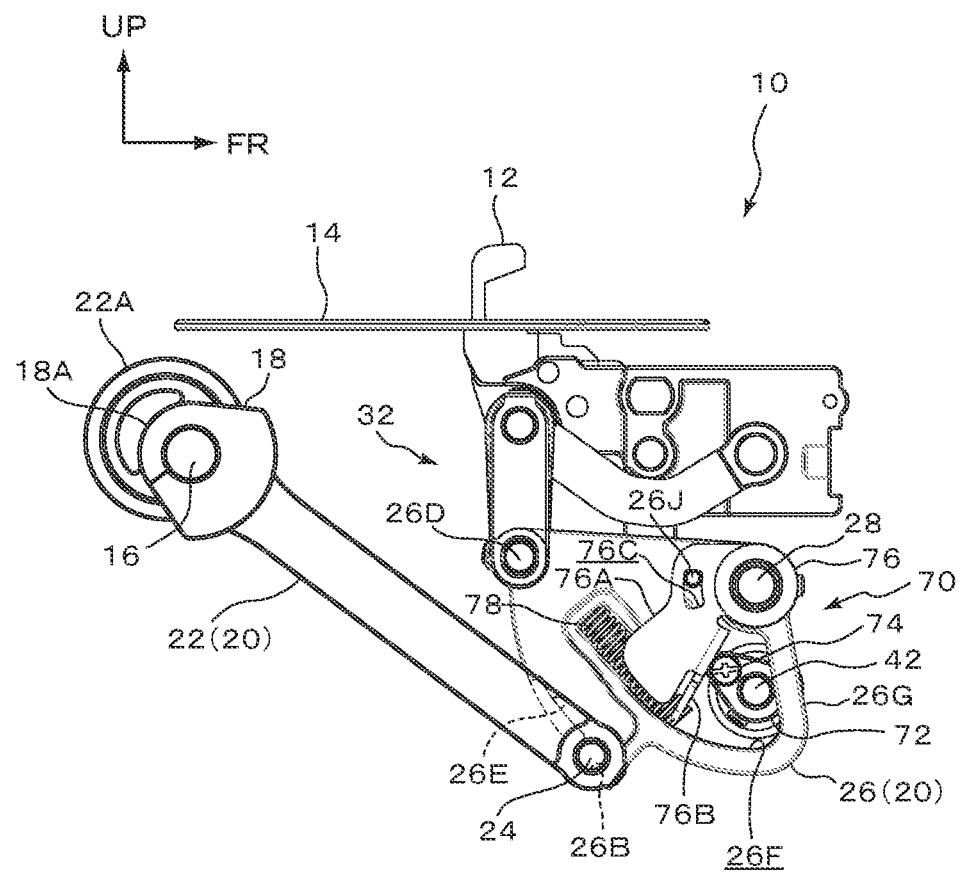
FIG. 9B is a side view as viewed from the left side showing the position switching mechanism in the state shown in FIG. 9A when the upper blade is switched to the interlock position.
Figure 10A:
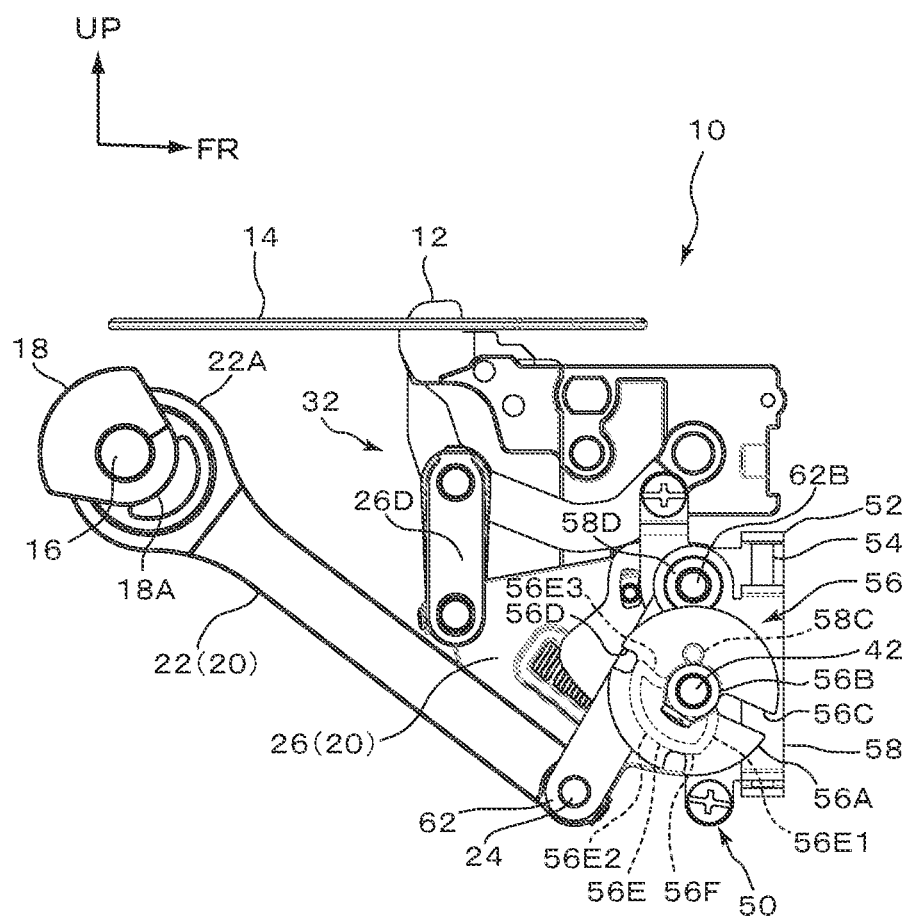
FIG. 10A is a side view as viewed from the left side showing the interlock switching mechanism when a blade cam shown in FIG. 9A is set to a position with an offset of 180 degrees around the axis of the main shaft.

Subsequently, as shown in FIGS. 8 through 10, in the state in which the rotational operation for the operating shaft 42 is enabled, the operating knob 44 (operating shaft 42) is turned in the rotational operation direction so as to operate the interlock switching mechanism 50 and the position switching mechanism 70. It should be noted that, in FIGS. 8 through 10, the left-side and right-side drawings show the operating shaft 42 at the same rotational phase as shown in FIGS. 4 through 7.

Subsequently, as shown in FIG. 8, the operating knob 44 is turned so as to turn the operating shaft 42 in the rotational operation direction from the state shown in FIG. 7. That is to say, the operating shaft 42 is turned in the same direction as when the overlock sewing machine 10 described above is switched from the interlock state to the interlock release state and the position of the upper blade 12 is switched from the interlock position to the retraction position.

Figure 8B:
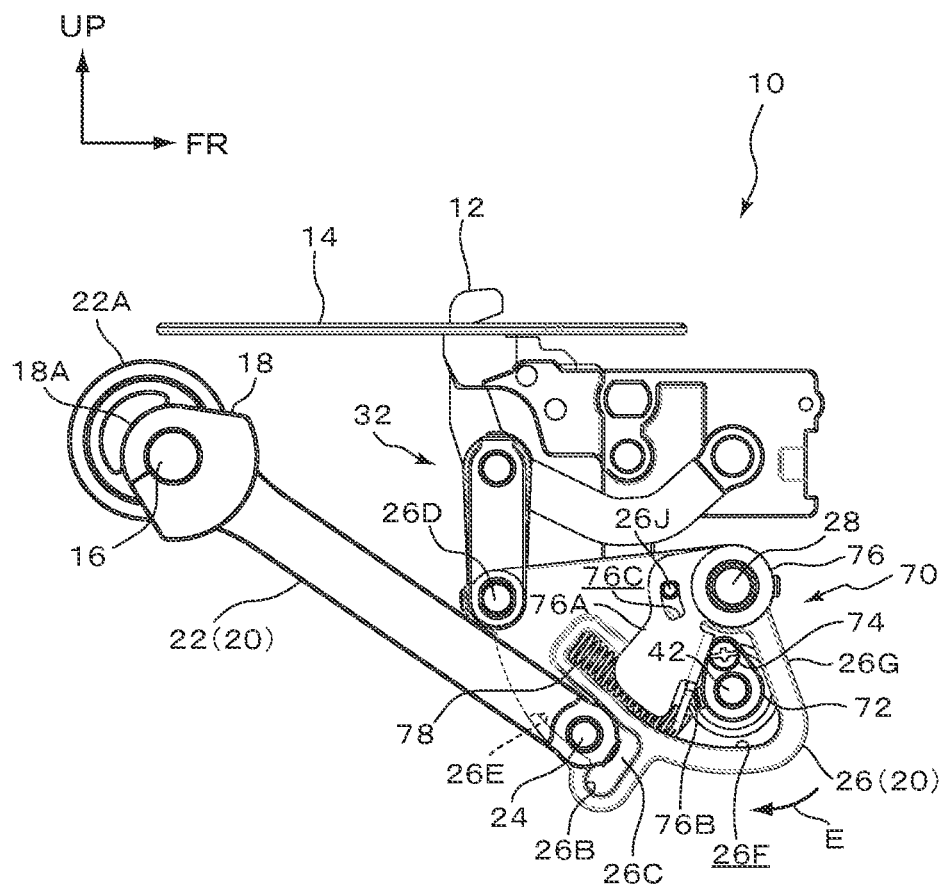
FIG. 8B is a side view as viewed from the left side showing the position switching mechanism in the state shown in FIG. 8A.

In this stage, as shown in FIG. 8B, in the position switching mechanism 70, the roller 74 of the position switching arm 72 is displaced toward the rear side such that it comes in contact with the curved portion 76B of the roller receiving plate 76. In this state, the roller 74 presses the roller receiving plate 76 toward the reverse swing side of the swing arm 26. Accordingly, the curved portion 76B of the roller receiving plate 76 presses the buffer spring 78 toward the reverse swing side of the swing arm 26. In this state, the buffer spring 78 presses the swing arm 26 toward the reverse swing side. In this operation, rotational force is applied to the swing arm 26 toward the reverse swing side.

Here, the buffer spring 78 is designed to have a spring load that is larger than the load required to swing the swing arm 26 toward the reverse swing side. Accordingly, upon further turning the position switching arm 72 in the rotational operation direction, the swing arm 26 is swung from the swing reverse position toward the reverse swing side (the side indicated by the arrow E in FIG. 8) in a state in which the buffer spring 78 is not operated (without compressive deformation of the buffer spring 78). In other words, the swing arm 26 is swung toward the reverse swing side by the buffer spring 78 in a state in which the roller receiving plate 76 is maintained at the hold position (in a state in which the relative position relation between the roller receiving plate 76 and the swing arm 26 is maintained). In this operation, the upper blade 12 coupled to the swing arm 26 is raised from the retraction position.

It should be noted that the roller receiving portion 26G is monolithically formed in the swing arm 26. Accordingly, when the swing arm 26 is swung toward the reverse swing side, the roller receiving portion 26G is also swung toward the reverse swing side together with the swing arm 26. That is to say, the swing arm 26 swings the roller receiving portion 26G toward the reverse swing side.

On the other hand, as shown in FIG. 8A, in the interlock switching mechanism 50, the cam 56 is turned in the rotational operation direction together with the operating shaft 42. In this stage, the second cam portion 56E2 of the cam 56 is displaced in the rotational operation direction with respect to the engagement pin 58C of the interlock switching plate 58, which releases a state in which the cam face 56F of the cam portion 56E and the engagement pin 58C are in contact. As a result, the interlock switching plate 58 is forced by the return spring 60 such that it is displaced downward, and accordingly, the rod pin 24 is forced such that it is displaced toward the lower side.

In this stage, the support portion 26E of the swing arm 26 is arranged on the lower side of and adjacent to the rod pin 24. Accordingly, with the position switching mechanism 70 described above, the swing arm 26 is swung toward the reverse swing side while the rod pin 24 is pressed in contact with the support portion 26E of the swing arm 26 such that the rod pin 24 is supported by the support portion 26E (the rod pin 24 is slid on the support portion 26E). With this arrangement, the displacement of the rod pin 24 toward the lower side is restricted. As a result, this arrangement restricts the downward displacement of the interlock switching plate 58 coupled to the rod pin 24 by the interlock switching arm 62, thereby maintaining the position of the interlock switching plate 58. That is to say, this arrangement maintains the position of the engagement pin 58C. With this arrangement, even after the contact state of the cam face 56F and the engagement pin 58C is released, the engagement pin 58C remains at the position shown in FIG. 8A (downward displacement of the interlock switching plate 58 due to the force applied by the return spring 60 is restricted).

Subsequently, as shown in FIG. 9, the operating knob 44 is turned so as to further turn the operating shaft 42 in the rotational operation direction from the state shown in FIG. 8.

As shown in FIG. 9B, in the position switching mechanism 70 in this state, the roller 74 of the position switching arm 72 is positioned diagonally upward toward the rear side with respect to the operating shaft 42. In this state, the swing arm 26 is set to the maximum reverse swing position by the roller receiving plate 76 pressed by the roller 74. In this operation, the upper blade 12 is further raised from the position shown in FIG. 8, and the position of the upper blade 12 is switched to the interlock position. It should be noted that, in this state, the support portion 26E of the swing arm 26 is displaced toward the reverse swing side with respect to the rod pin 24, which releases the contact state between the support portion 26E and the rod pin 24. By releasing the state of contact between the support portion 26E and the rod pin 24, this arrangement is set to a state in which the downward displacement of the rod pin 24 is enabled.

On the other hand, in the interlock switching mechanism 50, as described above, the state of contact between the engagement pin 58C of the interlock switching plate 58 and the cam portion 56E of the cam 56 has already been released. Furthermore, in this state as described above, the downward displacement of the rod pin 24 is enabled. Accordingly, as shown in FIG. 9A, in the interlock switching mechanism 50, the interlock switching plate 58 is lowered due to the force applied by the return spring 60. At the same time, the coupling pin 62B of the interlock switching arm 62 coupled to the interlock switching plate 58 is also lowered. As a result, the rod pin 24 coupled to the interlock switching arm 62 is inserted into the fitting groove 26B of the swing arm 26, thereby providing the fitting state between the rod pin 24 and the fitting groove 26B. Accordingly, the operation state is returned to the interlock state in which the main shaft 16 and the upper blade 12 operate together. At the same time, the upper blade 12 is set to the interlock position.

Furthermore, in this state, the engagement pin 58C of the interlock switching plate 58 comes in contact with the outer circumferential portion of the fixing cylinder portion 56B of the cam 56. Subsequently, the operating shaft 42 is further turned in the rotational operation direction until the cam 56 is set to the cam initial position and the roller 74 is set to the roller initial position. In this stage, the operation for the operating shaft 42 is completed. In this state, the operating shaft 42 is returned to a state before the operating shaft 42 is operated (i.e., the state shown in FIG. 4). That is to say, as viewed in a side view, the engagement pin 58C of the interlock switching plate 58 is set to a position that overlaps the first notch portion 56C of the cam 56. Accordingly, in this state, the movement of the cam main body 56A (i.e., operating shaft 42) toward the right side is enabled. In this operation, in the operating mechanism 40, the operating shaft 42 is slid toward the right side from the operation enabled position by the force applied by the force-applying spring 46, such that it is set to the operation restricted position. In this stage, the cam 56 is slid toward the right side together with the operating shaft 42, and the engagement pin 58C of the interlock switching plate 58 is inserted into the first notch portion 56C of the cam 56. As a result, the first notch portion 56C of the cam 56 and the engagement pin 58C are engaged again with each other at a position along the circumferential direction of the operating shaft 42. With such an arrangement, when the rotational operation for the operating shaft 42 is completed, the operation state is returned again to a state in which the rotational operation for the operating mechanism 40 is restricted.

With this arrangement, the upper blade rod 22 is coupled to the main shaft 16 by the blade cam 18, which allows the upper blade rod 22 to be swung by rotating the main shaft 16. That is to say, after the overlock sewing machine 10 is operated in the interlock released state, the swing position of the upper blade rod 22 changes according to the position of the blade cam 18 with respect to the main shaft 16. Accordingly, when the position of the upper blade 12 is switched from the retraction position to the interlock position by the position switching mechanism 70, the distance over which the swing arm 26 can be swung from the swing reverse position shown in FIG. 7B toward the reverse swing side changes according to the swing position of the upper blade rod 22.

Figure 10B:
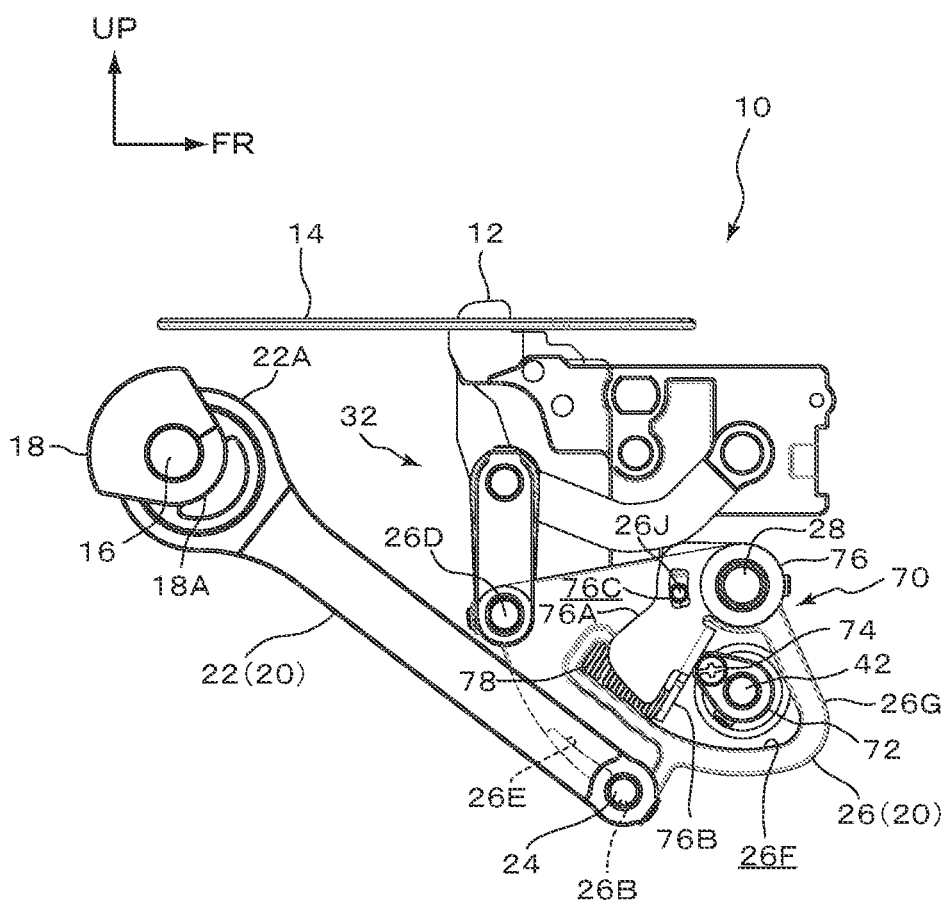
FIG. 10B is a side view as viewed from the left side showing the position switching mechanism in the state shown in FIG. 10A.

More specifically, in the state shown in FIG. 9B, the upper blade rod 22 is set to the maximum reverse swing position. Accordingly, when the upper blade rod 22 is positioned at the swing position shown in FIG. 9B, upon switching the position of the upper blade 12 to the interlock position by the position switching mechanism 70, the upper blade 12 is switched to the highest position in the interlock position range. In contrast, in the state shown in FIG. 10, the blade cam 18 is positioned with a phase offset of 180 degrees around the axis of the main shaft 16 as compared with the state shown in FIG. 9. That is to say, FIG. 10 shows the state in which the upper blade rod 22 is positioned in the maximum forward swing state. Accordingly, when the upper blade rod 22 is positioned at the swing position shown in FIG. 10B, upon switching the position of the upper blade 12 to the interlock position by the position switching mechanism 70, the upper blade 12 is switched to the lowest position in the interlock position range. As described above, when the position of the upper blade 12 is switched from the retraction position to the interlock position, the distance over which the swing arm 26 can be swung from the swing reverse position toward the reverse swing side changes according to the swing position of the upper blade rod 22. With the overlock sewing machine 10 according to the present embodiment, the buffer spring 78 of the position switching mechanism 70 is operated (subjected to compressive deformation) according to the swing position of the upper blade rod 22 so as to enable the operation of the position switching mechanism 70. Description will be made below regarding this point.

That is to say, in the state shown in FIG. 10B as described above, the distance over which the swing arm 26 can be swung from the swing reverse position toward the reverse swing side is shorter than that in the state shown in FIG. 9B. Accordingly, the position switching mechanism operates such that the roller 74 presses the roller receiving plate 76 such that the swing arm 26 reaches the position shown in FIG. 10B. In this state, the swinging of the swing arm 26 toward the reverse swing side is restricted by the upper blade rod 22. That is to say, the swinging of the buffer spring 78 engaged with the swing arm 26 is also restricted.

With such an arrangement in this state, the roller 74 is able to further press the roller receiving plate 76 according to the rotation of the operating shaft 42. Accordingly, in this state, upon further turning the operating shaft 42 in the rotational operation direction, the roller 74 further presses the other end portion of the buffer spring 78 via the curved portion 76B of the roller receiving plate 76. As a result, a compressive load is applied to the buffer spring 78 due to the pressure applied from the roller 74 (roller receiving plate 76). With such an arrangement, when the compressive load applied to the buffer spring 78 becomes equal to or greater than a predetermined value, compressive deformation occurs in the buffer spring 78 (the buffer spring 78 is operated), which relatively turns the roller receiving plate 76 from the hold position to the reverse swing side with respect to the swing arm 26. In this operation, the rotation of the roller 74 (operating shaft 42) in the rotational operating direction is enabled.

Subsequently, the relative rotation of the roller receiving plate 76 toward the reverse swing side with respect to the swing arm 26 continues according to the rotation of the operating shaft 42 in the rotational operation direction. As a result, the engagement pin 26J of the swing arm 26 is moved from the one end portion to the other end side of the engagement opening 76C of the roller receiving plate 76. With this, the pressing operation of the roller 74 for the roller receiving plate 76 ends (see FIG. 10B). Subsequently, upon further turning the operating shaft 42 in the rotational operation direction, the roller 74 is displaced toward the forward swing side with respect to the roller receiving plate 76. At the same time, the roller receiving plate 76 is relatively turned toward the forward swing side with respect to the swing arm 26 due to the force applied by the buffer spring 78. Furthermore, when the operating shaft 42 is turned until the roller 74 is set to the roller initial position, the roller 74 is shifted away from the roller receiving plate 76, and the roller receiving plate 76 is returned to the hold position. As described above, by operating the position switching mechanism 70 without suspension, this arrangement allows the position of the upper blade 12 to be switched from the retraction position to the interlock position regardless of the swing position of the upper blade 12.

As described above, with the overlock sewing machine 10 according to the present embodiment, by rotationally operating the operating shaft 42, the position switching mechanism 70 and the interlock switching mechanism 50 are operated. In the position switching mechanism 70, by pressing the roller receiving portion 26G of the swing arm by the roller 74, this arrangement allows the roller receiving portion 26G to swing the swing arm 26 toward the forward-swing side, which displaces the upper blade 12 from the interlock position to the retraction position. On the other hand, by pressing the roller receiving plate 76 and the buffer spring 78 by the roller 74, this arrangement allows the roller receiving plate 76 and the buffer spring 78 to swing the swing arm 26 toward the reverse swing side, which displaces the upper blade 12 from the retraction position to the driving position. Accordingly, when the position of the upper blade 12 is to be switched to the interlock position or otherwise the retraction position by the position switching mechanism 70, this arrangement allows the swing position of the swing arm 26 and the rotational phase of the operating shaft 42 to match each other. In other words, when the position of the upper blade 12 is to be switched to the interlock position or otherwise the retraction position, the swing position of the swing arm 26 can be controlled by the operating shaft 42. On the other hand, in the interlock switching mechanism 50, the other end portion (rod pin 24) of the upper blade rod 22 is displaced according to the rotational phase of the operating shaft 42 so as to switch the operating state to the interlock state or otherwise the interlock release state. Accordingly, this arrangement enables the position switching mechanism 50 to be configured to provide a timing at which the swing arm 26 is swung and a timing at which the other end portion of the upper blade rod 22 is displaced such that the swing timing and the displacement timing match each other in a simple manner. Accordingly, this arrangement allows the rod pin 24 to be satisfactorily fitted into the fitting groove 26B, thereby satisfactorily coupling the upper blade rod 22 and the swing arm 26. With this arrangement described above, the overlock sewing machine 10 can be satisfactorily returned from the interlock release state to the interlock state.

Furthermore, the position switching mechanism 70 is configured including the roller receiving plate 76 and the buffer spring 78. When the roller receiving plate 76 is pressed by the roller 74, the buffer spring 78 is operated (subjected to compressive deformation) according to the swing position of the upper blade rod 22 so as to adjust the relative position between the swing arm 26 and the roller receiving plate 76. With this arrangement, when the position of the upper blade 12 is switched from the retraction position to the interlock position by the position switching mechanism 70, this arrangement allows the operating shaft 42 to be rotationally operated, thereby allowing the position of the upper blade 12 to be immediately switched from the retraction position to the interlock position. This provides improved convenience for the user. Description will be made below regarding this point.

That is to say, if the position switching mechanism 70 does not include the roller receiving plate 76 and the buffer spring 78 and is configured such that the roller 74 directly presses the swing arm 26 (which will be referred to as a "comparison example" hereafter), when the upper blade rod 22 is set to the swing position shown in FIG. 10, the rotational operation for the operating shaft 42 is blocked before the operation state is switched. Specifically, when the roller 74 presses the swing arm 26, the reverse swinging of the swing arm 26 is restricted before the pressing operation of the roller 74 for the swing arm 26 is completed. This leads to an issue in that the rotational operation for the operating shaft 42 is blocked before the operation state is switched. Accordingly, in this case, such an arrangement requires the user to turn the main shaft 16 so as to set the upper blade rod 22 to the position shown in FIG. 9 in order to enable the rotational operation for the operating shaft 42. As a result, such an arrangement requires the user to turn the operating shaft 42 while turning the main shaft 16, which is a troublesome operation for the user, leading to degraded convenience for the user.

In contrast, with the present embodiment as described above, the position switching mechanism 70 is configured including the roller receiving plate 76 and the buffer spring 78. When the roller receiving plate 76 is pressed by the roller 74, the buffer spring 78 is operated (subjected to compressive deformation) according to the swing position of the upper blade rod 22 so as to adjust the relative position between the swing arm 26 and the roller receiving plate 76. Accordingly, even in a case in which the upper blade rod 22 is positioned at the position shown in FIG. 10, by adjusting the relative position between the swing arm 26 and the roller receiving plate 76 by the operation of the buffer spring 78, this arrangement enables the rotation of the operating shaft 42 in the rotational operating direction. With this arrangement, there is no need to turn the main shaft 16 so as to set the upper blade rod 22 to the position shown in FIG. 9, unlike the comparison example described above. This arrangement allows the position of the upper blade 12 to be immediately switched from the retraction position to the interlock position. In other words, such an arrangement requires the user to rotationally operate only the operating shaft 42 (operating knob 44) to switch the overlock sewing machine 10 from the interlock release state to the interlock state while switching the position of the upper blade 12 from the retraction position to the interlock position. Accordingly, this arrangement provides improved convenience for the user as compared with the above-described comparison example.

Furthermore, in the position switching mechanism 70, the buffer spring 78 is configured as a compression coil spring. This arrangement requires only a simple configuration to adjust the relative position between the swing arm 26 and the roller receiving plate 76.

Furthermore, the engagement opening 76C is formed in the roller receiving plate 76 in the form of a through hole such that it extends in the circumferential direction of the arm support shaft 28. The engagement pin 26J is formed in the swing arm 26 such that it is to be inserted into the engagement opening 76C. With such an arrangement, the roller receiving plate 76 is forced toward the forward swing side with respect to the swing arm 26 by the force applied by the buffer spring 78. In this state, the engagement pin 26J is engaged with one end portion of the engagement opening 76C. This arrangement allows the roller receiving plate 76 to be held at the hold position by the force applied by the buffer spring 78. With this arrangement, before the buffer spring 78 is operated, the roller receiving plate 76 can be swung together with the swing arm 26 as a single unit while holding the roller receiving plate 76 at the hold position.

Furthermore, in the interlock switching mechanism 50, the cam 56 is configured such that it can be rotated and slid together with the operating shaft 42 as a single unit. The first notch portion 56C is formed in the cam main body 56A of the cam 56. Furthermore, the interlock switching plate 58 is provided with the engagement pin 58C that can be engaged with the first notch portion 56C.

With such an arrangement, when the overlock sewing machine 10 is set to the interlock state, the operating shaft 42 is set to the operation restricted position. In this state, the engagement pin 58C is inserted into the first notch portion 56C, thereby engaging the engagement pin 58C with the first notch portion 56C at a position along the circumferential direction of the operating shaft 42. This restricts the rotational operation for the operating shaft 42. In contrast, when the operating shaft 42 is slid to the operation enabled position, the engagement pin 58C is detached from the first notch portion 56C, thereby releasing the engagement state between the engagement pin 58C and the first notch portion 56C. In this state, the rotational operation for the operating shaft 42 is enabled.

As described above, in the interlock state, before the user presses and displaces the operating shaft 42 toward the left side such that it is slid from the operation restricted position to the operation enabled position, the rotational operation for the operating shaft 42 is not enabled, which disables the operations of the position switching mechanism 70 and the interlock switching mechanism 50. Accordingly, in the interlock state of the overlock sewing machine 10, this arrangement is capable of preventing the overlock sewing machine 10 from being switched to the interlock release state and the position of the upper blade 12 from being switched to the retraction position without the user's intention.

Furthermore, the second notch portion 56D is formed in the cam main body 56A of the cam 56. The second notch portion 56D is configured such that it can be engaged with the engagement pin 58C of the interlock switching plate 58. With such an arrangement, in the interlock release state of the overlock sewing machine 10, upon setting the operating shaft 42 to the operation restricted position, the engagement pin 58C is inserted into the interior of the second notch portion 56D, thereby engaging the engagement pin 58C with the second notch portion 56D at a position along the circumferential direction of the operating shaft 42. In this state, the rotational operation for the operating shaft 42 is restricted. In contrast, upon sliding the operating shaft 42 to the operation enabled position, the engagement pin 58C is detached from the second notch portion 56D, thereby releasing the engagement state between the engagement pin 58C and the second notch portion 56D. In this operation, the rotational operation for the operating shaft 42 is enabled.

With this arrangement, as described above, in the interlock release state, before the user presses and displaces the operating shaft 42 toward the left side such that it is slid from the operation restricted position to the operation enabled position, the rotational operation for the operating shaft 42 is not enabled, which ensures that neither the position switching mechanism 70 nor the interlock switching mechanism 50 are operated. Accordingly, when the overlock sewing machine 10 is set to the interlock release state, this arrangement is capable of preventing the overlock sewing machine 10 from being switched to the interlock state and the position of the upper blade 12 from being switched to the interlock position without the user's intention.

Furthermore, the operating mechanism 40 includes the force-applying spring 46. The force-applying spring 46 forces the operating shaft 42 toward the right side (operation restricted position side).

Accordingly, for example, when the user turns the operating shaft 42 such that the position of the second notch portion 56D or otherwise the first notch portion 56C of the cam 56 matches the position of the engagement pin 58C, and the user removes the user's hand from the operating knob 44, the operating shaft 42 (cam 56) is slid toward the right side (operation restricted position side) due to the force applied by the force-applying spring 46. As a result, this arrangement allows the engagement pin 58C to be automatically engaged with the second notch portion 56D or otherwise the first notch portion 56C.

For example, in a case in which the user suspends the operation for pressing the operating shaft 42 toward the left side before the rotational operation for the operating knob 44 is completed, the operating shaft 42 (cam 56) is turned while the end of the engagement pin 58C is slid on the right-side face of the cam main body 56A. Subsequently, when the operating shaft 42 is turned such that the position of the second notch portion 56D or otherwise the first notch portion 56C of the cam 56 matches the position of the engagement pin 58C, the operating shaft 42 (cam 56) is slid toward the right side (operation restricted position side) due to the force applied by the force-applying spring 46. This arrangement allows the engagement pin 58C to be automatically engaged with the second notch portion 56D or otherwise the first notch portion 56C. Furthermore, this arrangement is capable of notifying the user of the completion of the rotational operation for the operating shaft 42.

Accordingly, this arrangement provides further improved convenience for the user.

When the overlock sewing machine 10 is to be switched from the interlock state to the interlock release state, the engagement pin 58C of the interlock switching plate 58 is slid on the cam face 56F of the cam 56, and the interlock switching plate 58 is displaced upward. In this operation, the rod pin 24 is displaced upward, which releases the fitting state between the rod pin 24 and the fitting groove 26B. Conversely, when the overlock sewing machine 10 is to be switched from the interlock release state to the interlock state, the interlock switching plate 58 is lowered by the force applied by the return spring 60 of the interlock switching mechanism 50. This displaces the rod pin 24 downward, which fits the rod pin 24 into the fitting groove 26B. That is to say, the interlock switching mechanism 50 employs a cam mechanism to allow the other end portion of the upper blade rod 22 to be displaced in the upper-lower direction. This arrangement requires only a simple configuration to allow the other end portion of the upper blade rod 22 to be displaced in the upper-lower direction.

Furthermore, the swing arm 26 is provided with the support portion 26E at a position adjacent to the fitting groove 26B. With such an arrangement, when the overlock sewing machine 10 is switched from the interlock release state to the interlock state, even after the state of contact between the cam portion 56E of the cam 56 and the engagement pin 58C is released, the swing arm 26 is swung toward the reverse swing side while the rod pin 24 is slid on the support portion 26E in a state in which they are in contact with each other. This arrangement is capable of maintaining the position of the interlock switching plate 58 coupled to the rod pin 24. That is to say, until the swing arm 26 is swung toward the reverse swing side, which is performed such that the rod pin 24 matches the fitting groove 26B of the swing arm 26 in a radial direction of the swing arm 26, this arrangement is capable of maintaining the interlock switching plate 58 in the non-operating state. In other words, the swing arm 26 is swung toward the reverse swing side such that the position of the rod pin 24 and the position of the fitting groove 26B of the swing arm 26 match each other in a radial direction of the swing arm 26. In this operation, the interlock switching plate 58 is displaced downward by the force applied by the return spring 60, which allows the rod pin 24 to be fitted into the interior of the fitting groove 26B. Accordingly, when the overlock sewing machine is to be switched from the interlock release state to the interlock state, this arrangement allows the rod pin 24 to be fitted into the interior of the fitting groove 26B in a sure manner.

Furthermore, in the interlock switching mechanism 50, the rod pin 24 and the interlock switching plate 58 are coupled by the interlock switching arm 62. In the interlock state of the overlock sewing machine 10, the coupling pin 62B of the interlock switching arm 62 is arranged on the same axis as the arm support shaft 28 which functions as the swing center of the swing arm 26. Accordingly, when the swing arm 26 is reciprocally swung around the axis of the arm support shaft 28, this arrangement allows the fitting position at which the rod pin 24 is fitted into the fitting groove 26B to be maintained at a constant position. In other words, in the reciprocal swinging operation of the swing arm 26 in a state in which the rod pin 24 is fitted into the fitting groove 26B, this arrangement is capable of suppressing deviation of the relative position relation between the rod pin 24 and the fitting groove 26B. This allows the stroke of the driving operation of the upper blade 12 in the upper-lower direction to be stabilized. Furthermore, this arrangement is capable of suppressing the occurrence of friction between the rod pin 24 and the fitting groove 26B. Accordingly, this arrangement is capable of suppressing the occurrence of abrasion in the rod pin 24 and the fitting groove 26B. Furthermore, this arrangement contributes to improvement of the durability of the rod pin 24 and the swing arm 26.

Furthermore, when the operating shaft 42 is not operated, the cam 56 is arranged such that its first notch portion 56C extends in the upper-lower direction such that the opening of the first notch portion 54C faces the upper side. With this arrangement, if the interlock switching plate 58 is displaced upward in the operation of the overlock sewing machine 10 in the interlock state, the engagement pin 58C of the interlock switching plate 58 is relatively displaced with respect to the first notch portion 56C along the longitudinal direction of the first notch portion 56C. In the operation of the overlock sewing machine 10 in the interlock state, this arrangement is capable of preventing the operating shaft 42 (i.e., operating knob 44) from rotating around the axis of the operating shaft 42.

It should be noted that description has been made in the present embodiment regarding an arrangement in which the upper blade rod 22 is provided with the rod pin 24, and the fitting groove 26B is formed in the swing arm 26. Also, a fitting groove may be formed in the upper blade rod 22, and the swing arm 26 may be provided with a fitting target shaft. In this case, an arrangement may be made in which the fitting groove of the upper blade rod 22 is configured in the form of a groove with its opening facing the lower side, and the one end portion of the interlock switching arm 62 is coupled to the other end portion of the upper blade rod 22. Also, in this case, the swing arm 26 may be provided with a support portion configured to slidably support the other end portion of the upper blade rod 22 in the interlock release state.

Furthermore, in the present embodiment, the buffer spring 78 of the position switching mechanism 70 is configured as a compression coil spring. However, the buffer spring 78 is not restricted to such a configuration. For example, the buffer spring 78 may be configured as a torsion spring. In this case, an arrangement may be made in which one end portion of the torsion spring is engaged with the swing arm 26, and the other end portion thereof is engaged with the roller receiving plate 76, so as to allow the torsion spring to force the roller receiving plate 76 toward the forward swing side.

Description has been in the present embodiment regarding an arrangement in which the roller receiving portion 26G that forms the position switching mechanism 70 is monolithically formed together with the swing arm 26. Also, the roller receiving portion 26G may be configured as a component separate from the swing arm 26. With such an arrangement, the roller receiving portion 26G and the swing arm 26 may be configured such that they can be swung as a single unit.

Description has been made in the present embodiment regarding an arrangement in which the force-applying spring of the operating mechanism 40 is configured as a compression spring. However, the force-applying spring 46 is not restricted to such an arrangement. For example, the force-applying spring 46 may be configured as a tension coil spring. Also, the operating shaft 42 may be configured such that it is forced toward the right side (operation restricted position side) by the force applied by the force-applying spring 46.

From the viewpoint that the overlock sewing machine 10 is required to operate such that it is not switched without the user's intention, the first notch portion 56C and the second notch portion 56D, each of which can be engaged with the engagement pin 58C of the interlock switching plate 58, may be formed in the cam 56. Also, the first notch portion 56C and the second notch portion 56D may be omitted from the cam 56. Also, either the first notch portion 56C or the second notch portion 56D may be omitted from the cam 56.

[Additional Statement]

Description has been made above regarding the present invention from the viewpoint that the overlock sewing machine is satisfactorily returned from the interlock release state to the interlock state. Also, the present invention can be understood from another viewpoint as follows.

That is to say, the overlock sewing machine described in the background technique is configured including: an upper blade driving unit including a rod and a second link unit (swing member) configured to drive an upper blade in the upper-lower direction; an interlock switching unit configured to switch the operation state between an interlock state in which the upper blade driving unit and the upper blade operate together and a release state in which the interlock state between the upper blade driving unit and the upper blade is released; an upper blade position switching unit configured to switch the position of the upper blade to a driving position (interlock position) or otherwise a retraction position; and an operating unit configured to synchronously operate the interlock switching unit and the upper blade position switching unit.

Furthermore, a notch is formed in the rod. When an engagement portion of the second link unit is engaged with the notch, the operating state is set to the interlock state. Furthermore, the upper blade position switching unit is monolithically formed together with the second link unit such that it can be rotated together with the second link unit as a single unit.

With such an arrangement, upon performing the rotational operation for the operating unit, the interlock switching unit and the upper blade position switching unit synchronously operate. In this operation, the operating state is switched to the interlock state or otherwise the release state, and the arrangement position of the upper blade is switched to the driving position or otherwise the retraction position.

However, with the above-described overlock sewing machine, in any state thereof, the operating unit can be rotationally operated at all times. Accordingly, for example, if the user inadvertently touches the operating unit, such an arrangement has the potential to cause an issue in that the state of the overlock sewing machine is switched and the arrangement position of the upper blade is switched without the user's intention.

In view of the above-described fact, it is a purpose of the present invention to provide an overlock sewing machine that is capable of preventing the state of the overlock sewing machine from switching to the interlock state or otherwise the interlock release state without the user's intention, and of preventing the position of the upper blade from switching to the interlock position or the retraction position without the user's intention.

A first embodiment for solving the above-described issue comprises:

an upper blade configured to be moved between a retraction position to which it is to be retracted downward with respect to the upper face of a needle plate and an interlock position defined on the upper side with respect to the retraction position;

a rod configured such that it extends in a direction that is orthogonal to the axial direction of a main shaft, and its one end portion is coupled to the main shaft by an eccentric cam, and such that it is swung by a driving force applied by the main shaft;

a swing member supported by a support shaft arranged in parallel with the axial direction of the main shaft such that it can be swung, coupled to the upper blade via another member, including a fitting portion configured such that it can be fitted into a fitting target portion provided to the other end portion of the rod, and configured such that, when the fitting portion is fitted into the fitting target portion, it is reciprocally swung accompanying the swinging of the rod according to the rotation of the main shaft so as to drive the upper blade in the upper-lower direction when the upper blade is set to the interlock position;

an interlock switching mechanism configured to switch the operating state to an interlock state in which the fitting target portion is fitted into the fitting portion so as to operate the upper blade together with the main shaft or otherwise an interlock release state in which the fitting state between the fitting target portion and the fitting portion is released so as to release the interlock state;

a position switching mechanism configured to operate so as to switch the position of the upper blade to the retraction position or otherwise the interlock position; and an operating shaft configured such that it can be slid between a first position and a second position to which it is to be slid from the first position in the axial direction, and such that, by turning the operating shaft, the interlock switching mechanism and the position switching mechanism are operated, wherein the interlock switching mechanism comprises:

a rotor provided such that it can be rotated together with the operating shaft as a single unit;

an interlock switching member coupled to the fitting target portion, including an engagement portion protruding toward the rotor side, and configured to operate according to the rotation of the rotor so as to switch the state to the interlock state or otherwise the interlock release state; and a first engagement target portion formed in the rotor such that it can be engaged with the engagement portion, wherein, in the interlock state, upon setting the operating shaft to the first position, the engagement portion is engaged with the first engagement target portion so as to restrict the rotation of the operating shaft, and wherein, upon sliding the operating shaft to the second position, the engagement state between the engagement portion and the first engagement target portion is released so as to enable the rotation of the operating shaft.

A second embodiment for solving the above-described issue relates to the overlock sewing machine according to the first embodiment. In the overlock sewing machine, a second engagement target portion is formed in the rotor such that it can be engaged with the engagement portion. In the interlock release state, upon setting the operating shaft to the first position, the engagement portion is engaged with the second engagement target portion so as to restrict the rotation of the operating shaft. Upon sliding the operating shaft to the second position, the engagement state between the engagement portion and the second engagement target portion is released so as to enable the rotation of the operating shaft.

A third embodiment for solving the above-described issue relates to the overlock sewing machine according to the first or the second embodiment. In the overlock sewing machine, the operating shaft is forced by a shaft force-applying member toward the first position side.

A fourth embodiment for solving the above-described issue relates to the overlock sewing machine according to any one of the first through the third embodiments. In the overlock sewing machine, the position switching mechanism comprises: a first switching portion provided such that it can be rotated together with the swing member as a single unit; a second switching portion provided on a reverse swing side of the swing member with respect to the first switching portion; and a pressing portion provided at a position that is eccentric with respect to the operating shaft such that it can be rotated together with the operating shaft as a single unit, and configured to be capable of pressing the first switching portion and the second switching portion. When the interlock state is set and the upper blade is set to the interlock position, upon turning the operating shaft toward one side around the axis of the operating shaft, the interlock switching mechanism displaces the other end portion of the rod so as to set the interlock release state, and the pressing portion presses the first switching portion such that the first switching portion swings the swing member toward a forward swing side, which moves the upper blade to the retraction position. When the interlock release state is set and the upper blade is set to the retraction position, upon turning the operating shaft toward the one side around the axis of the operating shaft, the pressing portion presses the second switching portion such that the second switching portion swings the swing member toward the reverse swing side, which moves the upper blade to the interlock position, and the interlock switching mechanism displaces the other end portion of the rod so as to set the interlock state.

DESCRIPTION OF THE REFERENCE NUMERALS

10 overlock sewing machine, 12 upper blade, 14 needle plate, 16 main shaft, 18 blade cam (eccentric cam), 18A eccentric cam portion, 20 driving mechanism, 22A circular portion, 22B fixing hole portion, 24 rod pin (fitting target portion, fitting target shaft), 26 swing arm (swing member), 26A bearing portion, 26B fitting groove (fitting portion), 26C communication groove, 26D connector portion, 26E support portion, 26F positioning hole, 26G roller receiving portion (first switching portion), 26H spring housing portion, 26J engagement pin, 28 arm support shaft (support shaft), 30 sewing machine housing, 32 link mechanism, 40 operating mechanism, 42 operating shaft, 44 operating knob, 44A knob portion, 46 force-applying spring (shaft force-applying member), 50 interlock switching mechanism, 52 holder, 52A fixing tab, 52B fixing opening, 52C fixing opening, 52DU support tab, 52DL support tab, 52EU support opening, 52EL support opening, 52F support opening, 52G support opening, 54 guide shaft, 54A shaft support portion, 56 cam (rotor), 56A cam main body, 56B fixing cylinder portion, 56C first notch portion (first engagement target portion), 56D second notch portion (second engagement target portion), 56E cam portion, 56E1 first cam portion, 56E2 second cam portion, 56E3 third cam portion, 56F cam face, 58 interlock switching plate (interlock switching member), 58AU guide tab, 58AL guide tab, 58B guide opening, 58C engagement pin (engagement portion), 58D bush, 60 return spring (switching force-applying member), 62 interlock switching arm, 62A coupling opening, 62B coupling pin, 70 position switching mechanism, 72 position switching arm, 72A fixing opening, 72B roller support shaft portion, 74 roller (pressing portion), 76 roller receiving plate (receiving member) (second switching portion), 76A plate main body, 76B curved portion, 76C engagement opening (slot), 78 buffer spring (adjustment member) (second switching portion), ER1 retaining ring, ER2 retaining ring, ER3 retaining ring, ER4 retaining ring, ER5 retaining ring, ER6 retaining ring, SW1 fixing screw, SW2 fixing screw, SW3 fixing screw.

What is claimed is:

1. An overlock sewing machine comprising:
an upper blade configured such that it can be moved between an interlock position at which it is driven in an upper-lower direction together with a rotation of a main shaft and a retraction position to which it is to be retracted downward from the interlock position;
a rod configured such that it extends in a direction that is orthogonal to an axial direction of the main shaft, and arranged such that one end portion is coupled to the main shaft by an eccentric cam, which allows the rod to be swung by a driving force applied by the main shaft;
a swing member supported by a support shaft arranged in parallel with the axial direction of the main shaft such that it can be swung, coupled to the upper blade via another member, comprising a fitting portion configured such that it can be fitted into a fitting target portion provided to the other end portion of the rod, and configured such that, when the fitting portion is fitted into the fitting target portion, the swing member is reciprocally swung accompanying a swinging of the rod according to a rotation of the main shaft, so as to drive the upper blade in the upper-lower direction when the upper blade is set to the interlock position;
an interlock switching mechanism configured to operate to switch a state to an interlock state, in which the fitting target portion is fitted into the fitting portion so as to allow the upper blade to be driven together with the main shaft, or otherwise an interlock release state, in which a fitting state between the fitting target portion and the fitting portion is released so as to release the interlock state;
a position switching mechanism configured to operate such that a position of the upper blade is switched to the retraction position or otherwise the interlock position; and
an operating shaft configured such that it can be slid between a first position and a second position to which it is to be slid from the first position in the axial direction, and such that, by turning the operating shaft, the interlock switching mechanism and the position switching mechanism are operated,
wherein the interlock switching mechanism comprises:
a rotor provided such that it can be rotated together with the operating shaft as a single unit;
an interlock switching member coupled to the fitting target portion, including an engagement portion protruding toward a rotor side, and configured to operate according to the rotation of the rotor so as to switch the state to the interlock state or otherwise the interlock release state; and
a first engagement target portion formed in the rotor such that it can be engaged with the engagement portion,
wherein, in the interlock state, upon setting the operating shaft to the first position, the engagement portion is engaged with the first engagement target portion so as to restrict the rotation of the operating shaft, and wherein, upon sliding the operating shaft to the second position, the engagement state between the engagement portion and the first engagement target portion is released so as to enable the rotation of the operating shaft.

2. The overlock sewing machine according to claim 1, wherein the interlock switching mechanism comprises a coupling member configured to couple the fitting target portion and the interlock switching member, wherein the fitting target portion is rotatably coupled to one end portion of the coupling member, and the other end portion of the coupling member is provided with a coupling pin rotatably supported by the interlock switching member, and wherein, when the interlock state is set, the coupling pin is arranged on the same axis as that of the support shaft.

3. The overlock sewing machine according to claim 1, wherein the interlock switching member is configured such that it can be relatively moved with respect to the rotor in the upper-lower direction, wherein the first fitting target portion is formed in a groove structure such that it extends in the upper-lower direction and has an opening that faces an upper side in the interlock state, wherein, in the interlock state, upon setting the operating shaft to the first position, the engagement portion is inserted into an interior of the first engagement target portion, and wherein, in the interlock state, upon sliding the operating shaft to the second position and turning the rotor, the interlock switching member is displaced upward so as to release the fitting state between the fitting target portion and the fitting portion.

4. The overlock sewing machine according to claim 1, wherein a second engagement target portion is formed in the rotor such that it can be engaged with the engagement portion, wherein, in the interlock release state, by setting the operating shaft to the first position, the engagement portion is engaged with the second engagement target portion so as to restrict the rotation of the operating shaft, and wherein, upon sliding the operating shaft to the second position, the engagement state between the engagement portion and the second engagement portion is released, which enables the rotation of the operating shaft.

5. The overlock sewing machine according to claim 4, wherein the second engagement target portion is formed in a groove structure having an opening that faces the outer side in a radial direction of the rotor, and is arranged with an offset along a circumferential direction of the rotor with respect to the first engagement target portion, and wherein, in the interlock release state, by setting the operating shaft to the first position, the engagement portion is inserted into an interior of the second engagement target portion.

6. The overlock sewing machine according to claim 1, wherein the operating shaft is forced toward the first position side by a shaft force-applying member.

7. The overlock sewing machine according to claim 1, wherein the operating shaft is configured to be turned in the same rotational direction when the interlock switching mechanism is to be operated so as to switch the state from the interlock state to the interlock release state and the position switching mechanism is to be operated so as to switch the position from the interlock position to the retraction position, as well as when the interlock switching mechanism is to be operated so as to switch the state from the interlock release state to the interlock state and the position switching mechanism is to be operated so as to switch the position from the retraction position to the interlock position.

* * * * *